United States Patent
Langlois

(10) Patent No.: US 9,060,884 B2
(45) Date of Patent: Jun. 23, 2015

(54) IMPEDANCE SIMULATING MOTION CONTROLLER FOR ORTHOTIC AND PROSTHETIC APPLICATIONS

(75) Inventor: David Langlois, Quebec (CA)

(73) Assignee: Victhom Human Bionics Inc., Quebec (CA)

( * ) Notice: Subject to any disclaimer, the term of this patent is extended or adjusted under 35 U.S.C. 154(b) by 231 days.

(21) Appl. No.: 13/099,961

(22) Filed: May 3, 2011

(65) Prior Publication Data

US 2012/0283844 A1    Nov. 8, 2012

(51) Int. Cl.
| | | |
|---|---|---|
| A61F 2/68 | (2006.01) | |
| A61F 5/01 | (2006.01) | |
| A61F 2/70 | (2006.01) | |
| A61F 2/76 | (2006.01) | |

(52) U.S. Cl.
CPC .............. *A61F 2/68* (2013.01); *A61F 5/0102* (2013.01); *A61F 2002/701* (2013.01); *A61F 2002/7615* (2013.01); *A61F 2002/7625* (2013.01); *A61F 2002/7635* (2013.01); *A61F 2002/764* (2013.01)

(58) Field of Classification Search
CPC ........................... A61F 2/68; A61F 2002/7625
USPC ...................................................... 623/24, 50
See application file for complete search history.

(56) References Cited

U.S. PATENT DOCUMENTS

| | | | |
|---|---|---|---|
| 909,859 | A | 1/1909 | Apgar |
| 1,951,622 | A | 3/1934 | McElroy |
| 2,568,051 | A | 9/1951 | Catranis |
| 2,619,652 | A | 12/1952 | Vesper |
| 2,859,451 | A | 11/1958 | Mauch |
| 3,022,400 | A | 2/1962 | Ahlefeldt |
| 3,316,558 | A | 5/1967 | Mortensen |
| 3,417,409 | A | 12/1968 | Prahl |
| 3,501,776 | A | 3/1970 | Beeker et al. |
| 3,579,276 | A | 5/1971 | Newell |
| 3,678,311 | A | 7/1972 | Mattingly |
| 3,701,368 | A | 10/1972 | Stern |
| 3,791,375 | A | 2/1974 | Pfeifer |

(Continued)

FOREIGN PATENT DOCUMENTS

| | | |
|---|---|---|
| CA | 2405356 | 10/2001 |
| CA | 2494365 | 3/2004 |

(Continued)

OTHER PUBLICATIONS

Perry, Jacquelin, MD, Gait Analysis: Normal and Pathological Function, Ch. 5, pp. 92-108, 1992.

(Continued)

*Primary Examiner* — Bruce E Snow
(74) *Attorney, Agent, or Firm* — Knobbe Martens Olson & Bear LLP

(57) ABSTRACT

An impedance simulating motion controller for orthotic and prosthetic devices includes an equilibrium trajectory generator that receives locomotion data regarding the locomotion of a user, a dynamic trajectory compensator that generates one or more control parameters based on the locomotion data and one or more physiological characteristics of the user, and a dynamic gain tuner that adjusts the one or more control parameters based on a gain scaling factor that is calculated using a measured deflection point and an expected deflection point. The adjusted control parameters are used to control movement of an actuator of an orthotic or prosthetic device.

14 Claims, 21 Drawing Sheets

(56) References Cited

U.S. PATENT DOCUMENTS

| | | |
|---|---|---|
| 3,820,168 A | 6/1974 | Horvath |
| 3,995,324 A | 12/1976 | Burch |
| 4,030,141 A | 6/1977 | Graupe |
| 4,152,787 A | 5/1979 | Meggyesy |
| 4,179,759 A | 12/1979 | Smith |
| 4,398,109 A | 8/1983 | Kuwako et al. |
| 4,420,714 A | 12/1983 | Petersen et al. |
| 4,441,644 A | 4/1984 | Farian |
| 4,501,981 A | 2/1985 | Hansen |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,579,558 A | 4/1986 | Ramer |
| 4,600,357 A | 7/1986 | Coules |
| 4,649,934 A | 3/1987 | Fraser et al. |
| 4,711,242 A | 12/1987 | Petrofsky |
| 4,726,404 A | 2/1988 | Haber et al. |
| 4,730,625 A | 3/1988 | Fraser et al. |
| 4,770,662 A | 9/1988 | Giampapa |
| 4,776,852 A | 10/1988 | Bubic |
| 4,790,522 A | 12/1988 | Drutchas |
| 4,805,455 A | 2/1989 | DelGiorno et al. |
| 4,814,661 A | 3/1989 | Ratzlaff et al. |
| 4,843,921 A | 7/1989 | Kremer |
| 4,854,428 A | 8/1989 | Horvath |
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards |
| 5,033,291 A | 7/1991 | Podoloff et al. |
| 5,044,360 A | 9/1991 | Janke |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,181,931 A | 1/1993 | Van de Veen |
| 5,200,679 A | 4/1993 | Graham |
| 5,201,772 A | 4/1993 | Maxwell |
| 5,217,500 A | 6/1993 | Phillips |
| 5,219,365 A | 6/1993 | Sabolich |
| 5,246,465 A | 9/1993 | Rincoe et al. |
| 5,252,102 A | 10/1993 | Singer et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,299,454 A | 4/1994 | Fuglewicz et al. |
| 5,314,498 A | 5/1994 | Gramnäs |
| 5,323,650 A | 6/1994 | Fullen et al. |
| 5,336,269 A | 8/1994 | Smits |
| 5,357,696 A | 10/1994 | Gray et al. |
| 5,376,133 A | 12/1994 | Gramnas |
| 5,376,137 A | 12/1994 | Shorter et al. |
| 5,383,939 A | 1/1995 | James |
| 5,387,246 A | 2/1995 | Phillips |
| 5,405,407 A | 4/1995 | Kodama et al. |
| 5,405,409 A | 4/1995 | Knoth |
| 5,405,410 A | 4/1995 | Arbogast et al. |
| 5,406,845 A | 4/1995 | Berger et al. |
| 5,408,873 A | 4/1995 | Schmidt et al. |
| 5,443,528 A | 8/1995 | Allen |
| 5,486,209 A | 1/1996 | Phillips |
| 5,545,232 A | 8/1996 | Van de Veen |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,213 A | 11/1996 | Allen |
| 5,583,476 A | 12/1996 | Langford |
| 5,632,725 A | 5/1997 | Silver et al. |
| 5,642,096 A | 6/1997 | Leyerer et al. |
| 5,650,704 A | 7/1997 | Pratt et al. |
| 5,678,448 A | 10/1997 | Fullen et al. |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,725,598 A | 3/1998 | Phillips |
| 5,728,170 A | 3/1998 | Becker et al. |
| 5,746,774 A | 5/1998 | Kramer et al. |
| 5,751,083 A | 5/1998 | Tamura et al. |
| 5,779,735 A | 7/1998 | Molino |
| 5,800,568 A | 9/1998 | Atkinson et al. |
| 5,888,212 A | 3/1999 | Petrofsky et al. |
| 5,888,213 A | 3/1999 | Sears et al. |
| 5,888,236 A | 3/1999 | van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,929,332 A | 7/1999 | Brown |
| 5,953,683 A | 9/1999 | Hansen et al. |
| 5,955,667 A | 9/1999 | Fyfe |
| 5,957,981 A | 9/1999 | Gramnas |
| 5,972,035 A | 10/1999 | Blatchford |
| 5,982,156 A | 11/1999 | Weimer et al. |
| 5,984,972 A | 11/1999 | Huston et al. |
| 5,998,930 A | 12/1999 | Upadhyay et al. |
| 6,006,412 A | 12/1999 | Bergmann et al. |
| 6,007,582 A | 12/1999 | May |
| 6,039,091 A | 3/2000 | Rodgers et al. |
| 6,061,577 A | 5/2000 | Andrieu et al. |
| 6,091,977 A | 7/2000 | Tarjan et al. |
| 6,095,486 A | 8/2000 | Ivers et al. |
| 6,113,642 A | 9/2000 | Petrofsky et al. |
| 6,122,960 A | 9/2000 | Hutchings et al. |
| 6,129,766 A | 10/2000 | Johnson et al. |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,379,393 B1 | 4/2002 | Mavroidis et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,138 B1 | 12/2002 | Irby et al. |
| 6,500,210 B1 | 12/2002 | Sabolich et al. |
| 6,513,381 B2 | 2/2003 | Fyfe et al. |
| 6,517,503 B1 | 2/2003 | Naft et al. |
| 6,517,585 B1 | 2/2003 | Zahedi et al. |
| 6,522,266 B1 | 2/2003 | Soehren et al. |
| 6,587,728 B2 | 7/2003 | Fang et al. |
| 6,589,287 B2 | 7/2003 | Lundborg |
| 6,602,295 B1 | 8/2003 | Doddroe et al. |
| 6,610,101 B2 | 8/2003 | Herr et al. |
| 6,613,097 B1 | 9/2003 | Cooper |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |

(56) References Cited

U.S. PATENT DOCUMENTS

| | | |
|---|---|---|
| 6,704,024 B2 | 3/2004 | Robotham et al. |
| 6,704,582 B2 | 3/2004 | Le-Faucheur et al. |
| 6,733,180 B2 | 5/2004 | Nakamura |
| 6,740,125 B2 | 5/2004 | Mosler |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,770,045 B2 | 8/2004 | Naft et al. |
| 6,805,677 B2 | 10/2004 | Simmons |
| 6,811,571 B1 | 11/2004 | Phillips |
| 6,813,582 B2 | 11/2004 | Levi et al. |
| 6,824,569 B2 | 11/2004 | Okediji |
| D499,487 S | 12/2004 | Bedard et al. |
| D501,925 S | 2/2005 | Bedard et al. |
| 6,855,170 B2 | 2/2005 | Gramnas |
| 6,875,241 B2 | 4/2005 | Christensen |
| 6,876,135 B2 | 4/2005 | Pelrine et al. |
| 6,918,308 B2 | 7/2005 | Biedermann |
| 6,955,692 B2 | 10/2005 | Grundei |
| 6,966,882 B2 | 11/2005 | Horst |
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,964 B2 | 6/2006 | Wild |
| 7,091,679 B2 | 8/2006 | Schroeder et al. |
| 7,118,601 B2 | 10/2006 | Yasui et al. |
| 7,131,998 B2 | 11/2006 | Pasolini |
| 7,137,998 B2 | 11/2006 | Bedard |
| 7,147,667 B2 | 12/2006 | Bedard |
| 7,164,967 B2 | 1/2007 | Etienne-Cummings et al. |
| 7,190,096 B2 | 3/2007 | Blanding et al. |
| 7,198,071 B2 | 4/2007 | Bisbee, III et al. |
| 7,279,009 B2 | 10/2007 | Herr |
| 7,308,333 B2 | 12/2007 | Kern et al. |
| 7,313,463 B2 | 12/2007 | Herr et al. |
| 7,314,490 B2 | 1/2008 | Bedard et al. |
| 7,393,364 B2 | 7/2008 | Martin |
| 7,410,338 B2 | 8/2008 | Schiele et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,475,606 B2 | 1/2009 | Selig et al. |
| 7,485,152 B2 | 2/2009 | Haynes et al. |
| 7,500,407 B2 | 3/2009 | Boiten |
| 7,503,900 B2 | 3/2009 | Goswami |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,597,017 B2 | 10/2009 | Bédard et al. |
| 7,602,301 B1 | 10/2009 | Stirling et al. |
| 7,611,543 B2 | 11/2009 | Townsend et al. |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,731,759 B2 | 6/2010 | Pusch et al. |
| 7,736,394 B2 | 6/2010 | Bedard et al. |
| 7,780,741 B2 | 8/2010 | Janusson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| 7,815,689 B2 | 10/2010 | Bedard et al. |
| 7,862,620 B2 | 1/2011 | Clausen et al. |
| 7,867,284 B2 | 1/2011 | Bedard |
| 7,867,285 B2 | 1/2011 | Clausen et al. |
| 7,883,546 B2 | 2/2011 | Kazerooni et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,953,549 B2 | 5/2011 | Graham et al. |
| 7,955,398 B2 | 6/2011 | Bedard et al. |
| 8,007,544 B2 | 8/2011 | Jonsson et al. |
| RE42,903 E | 11/2011 | Deffenbaugh et al. |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,122,772 B2 | 2/2012 | Clausen et al. |
| 8,142,370 B2 | 3/2012 | Weinberg et al. |
| 8,211,042 B2 | 7/2012 | Gilbert et al. |
| 8,231,687 B2 | 7/2012 | Bedard et al. |
| 8,366,788 B2 | 2/2013 | Moser et al. |
| 8,403,997 B2 | 3/2013 | Sykes et al. |
| 8,435,309 B2 | 5/2013 | Gilbert et al. |
| 8,500,823 B2 | 8/2013 | Herr et al. |
| 8,555,715 B2 | 10/2013 | Langlois et al. |
| 8,617,254 B2 | 12/2013 | Bisbee, III et al. |
| 8,709,097 B2 | 4/2014 | Jonsson et al. |
| 8,869,626 B2 | 10/2014 | Clausen et al. |
| 2001/0020143 A1 | 9/2001 | Stark et al. |
| 2001/0029400 A1 | 10/2001 | Deffenbaugh et al. |
| 2002/0043880 A1 | 4/2002 | Suzuki et al. |
| 2002/0087213 A1 | 7/2002 | Bertram |
| 2002/0087216 A1 | 7/2002 | Atkinson et al. |
| 2002/0094919 A1 | 7/2002 | Rennex et al. |
| 2002/0180572 A1 | 12/2002 | Kakehashi et al. |
| 2004/0049291 A1 | 3/2004 | Deharde et al. |
| 2004/0064195 A1 | 4/2004 | Herr |
| 2004/0086240 A1 | 5/2004 | Togami et al. |
| 2004/0153484 A1 | 8/2004 | Unno |
| 2004/0217324 A1 | 11/2004 | Hsu et al. |
| 2005/0010139 A1 | 1/2005 | Aminian et al. |
| 2005/0029979 A1 | 2/2005 | Lee et al. |
| 2005/0049719 A1 | 3/2005 | Wilson |
| 2005/0107889 A1 | 5/2005 | Bedard et al. |
| 2005/0131317 A1 | 6/2005 | Oddsson et al. |
| 2005/0137717 A1 | 6/2005 | Gramnas et al. |
| 2005/0216097 A1 | 9/2005 | Rifkin |
| 2005/0283257 A1 | 12/2005 | Bisbee et al. |
| 2006/0069336 A1 | 3/2006 | Krebs et al. |
| 2006/0122711 A1 | 6/2006 | Bedard et al. |
| 2006/0135883 A1 | 6/2006 | Jonsson et al. |
| 2006/0136072 A1 | 6/2006 | Bisbee et al. |
| 2006/0173552 A1 | 8/2006 | Roy |
| 2006/0184252 A1 | 8/2006 | Oddsson et al. |
| 2006/0184280 A1 | 8/2006 | Oddsson et al. |
| 2006/0249315 A1 | 11/2006 | Herr et al. |
| 2006/0259153 A1 | 11/2006 | Harn et al. |
| 2007/0027557 A1 | 2/2007 | Jonsson et al. |
| 2007/0032748 A1 | 2/2007 | McNeil et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2007/0233279 A1 | 10/2007 | Kazerooni et al. |
| 2007/0270722 A1 | 11/2007 | Loeb et al. |
| 2008/0046096 A1 | 2/2008 | Bedard et al. |
| 2008/0114272 A1* | 5/2008 | Herr et al. .............. 600/595 |
| 2008/0122303 A1 | 5/2008 | Santo et al. |
| 2008/0133171 A1 | 6/2008 | Feichtinger et al. |
| 2009/0024062 A1 | 1/2009 | Einarsson |
| 2009/0030344 A1 | 1/2009 | Moser et al. |
| 2009/0056445 A1 | 3/2009 | Veltink |
| 2009/0171469 A1 | 7/2009 | Thorsteinsson et al. |
| 2009/0265018 A1 | 10/2009 | Goldfarb et al. |
| 2009/0299480 A1 | 12/2009 | Gilbert et al. |
| 2009/0312844 A1 | 12/2009 | Ikeuchi et al. |
| 2010/0023133 A1 | 1/2010 | Fairbanks et al. |
| 2010/0042256 A1 | 2/2010 | Takenaka et al. |
| 2010/0063778 A1 | 3/2010 | Schrock et al. |
| 2010/0113980 A1* | 5/2010 | Herr et al. .............. 600/587 |
| 2010/0114329 A1 | 5/2010 | Casler et al. |
| 2010/0131101 A1 | 5/2010 | Engeberg et al. |
| 2010/0160844 A1 | 6/2010 | Gilbert et al. |
| 2010/0174385 A1 | 7/2010 | Casler et al. |
| 2010/0179668 A1 | 7/2010 | Herr et al. |
| 2010/0262260 A1 | 10/2010 | Bédard et al. |
| 2010/0286796 A1 | 11/2010 | Clausen |
| 2010/0305716 A1 | 12/2010 | Pusch et al. |

(56) References Cited

U.S. PATENT DOCUMENTS

| | | |
|---|---|---|
| 2010/0324698 A1 | 12/2010 | Sverrisson et al. |
| 2010/0324699 A1 | 12/2010 | Herr et al. |
| 2011/0125290 A1 | 5/2011 | Langlois |
| 2011/0257764 A1 | 10/2011 | Herr et al. |
| 2011/0264230 A1 | 10/2011 | Herr et al. |
| 2011/0295384 A1 | 12/2011 | Herr et al. |
| 2011/0295385 A1 | 12/2011 | Herr et al. |
| 2013/0095861 A1 | 4/2013 | Li et al. |
| 2013/0158444 A1 | 6/2013 | Herr et al. |
| 2013/0261766 A1 | 10/2013 | Langlois et al. |
| 2013/0268093 A1 | 10/2013 | Gilbert et al. |
| 2013/0311133 A1 | 11/2013 | Kordari et al. |
| 2013/0311134 A1 | 11/2013 | Kordari et al. |
| 2014/0156025 A1 | 6/2014 | Bisbee, III et al. |
| 2014/0200680 A1 | 7/2014 | Holgate et al. |
| 2014/0324190 A1 | 10/2014 | Jonsson et al. |

FOREIGN PATENT DOCUMENTS

| | | |
|---|---|---|
| CA | 2543061 | 6/2005 |
| CA | 2546858 | 6/2005 |
| CN | 2043873 | 9/1989 |
| CN | 1074109 | 7/1993 |
| CN | 1215614 | 5/1999 |
| CN | 1376856 | 10/2002 |
| DE | 3543291 | 6/1987 |
| DE | 4305213 | 8/1993 |
| DE | 4229330 | 3/1994 |
| DE | 4318901 | 1/1995 |
| DE | 195 21 464 | 3/1997 |
| DE | 19754690 | 7/1999 |
| DE | 19859931 | 7/2000 |
| EP | 0 380 060 | 8/1990 |
| EP | 0503775 | 9/1992 |
| EP | 0549855 | 7/1993 |
| EP | 0628296 | 12/1994 |
| EP | 0718951 | 6/1996 |
| EP | 0902547 | 3/1999 |
| EP | 1066 793 | 1/2001 |
| EP | 1125825 | 1/2001 |
| EP | 1107420 | 6/2001 |
| EP | 1166726 | 1/2002 |
| EP | 1169982 | 1/2002 |
| EP | 1340478 | 9/2003 |
| EP | 1 792 597 | 6/2007 |
| EP | 1531767 | 12/2008 |
| EP | 2 621 414 | 8/2013 |
| FR | 2293185 | 7/1976 |
| FR | 2623086 | 5/1989 |
| GB | 1 191 633 | 5/1970 |
| GB | 2201260 | 8/1988 |
| GB | 2 244 006 | 11/1991 |
| GB | 2260495 A | 4/1993 |
| GB | 2 268 070 A | 1/1994 |
| GB | 2 301 776 | 12/1996 |
| GB | 2 302 949 | 2/1997 |
| GB | 2 328 160 | 2/1999 |
| GB | 2 334 891 | 9/1999 |
| GB | 2 338 653 | 12/1999 |
| GB | 2 343 848 | 5/2000 |
| GB | 2 367 753 | 4/2002 |
| JP | 59/32453 | 2/1984 |
| JP | 59-071747 | 4/1984 |
| JP | 59/71747 | 4/1984 |
| JP | 60081530 | 5/1985 |
| JP | 11056885 | 3/1999 |
| JP | 11000345 | 6/1999 |
| JP | 2001/277175 | 10/2001 |
| JP | 2002-191654 | 7/2002 |
| JP | 2002-533161 | 10/2002 |
| JP | 2003/250824 | 9/2003 |
| JP | 2005-500 | 1/2005 |
| SU | 1447366 | 12/1988 |
| WO | WO 93-24080 A1 | 12/1993 |
| WO | WO 94/06374 | 3/1994 |
| WO | WO 94/09727 A2 | 5/1994 |
| WO | WO 95/26171 | 10/1995 |
| WO | WO 96/41598 | 12/1996 |
| WO | WO 96/41599 | 12/1996 |
| WO | WO 97/00661 | 1/1997 |
| WO | WO 98/25552 | 6/1998 |
| WO | WO 98/38951 | 9/1998 |
| WO | WO 99/05991 | 2/1999 |
| WO | WO 99/08621 | 2/1999 |
| WO | WO 99/29272 | 6/1999 |
| WO | WO 00/27318 | 5/2000 |
| WO | WO 00/30572 | 6/2000 |
| WO | WO 00/38599 | 7/2000 |
| WO | WO 01/17466 | 3/2001 |
| WO | WO 01/54630 | 8/2001 |
| WO | WO 01/72245 | 10/2001 |
| WO | WO 02/080825 | 10/2002 |
| WO | WO 03/003953 | 1/2003 |
| WO | WO 03/086245 | 10/2003 |
| WO | WO 03/088373 | 10/2003 |
| WO | WO 2004/017871 | 3/2004 |
| WO | WO 2004/017873 | 3/2004 |
| WO | WO 2004/100191 | 11/2004 |
| WO | WO 2005/041819 | 5/2005 |
| WO | WO 2005/048887 | 6/2005 |
| WO | WO 2005/051248 | 6/2005 |
| WO | WO 2005/087144 | 9/2005 |
| WO | WO 2005/110293 | 11/2005 |
| WO | WO 2006/024876 | 3/2006 |
| WO | WO 2006/083913 | 8/2006 |
| WO | WO 2007/025116 | 3/2007 |
| WO | WO 2007/027668 | 3/2007 |
| WO | WO 2010/027968 | 3/2010 |
| WO | WO 2011/100117 | 8/2011 |
| WO | WO 2011/100118 | 8/2011 |
| WO | WO 2012/047721 | 4/2012 |
| WO | WO 2012/150500 | 11/2012 |
| WO | WO 2013/148726 | 10/2013 |

OTHER PUBLICATIONS

Diginfo TV, "Powered Prosthetic Thigh and Leg", uploaded Nov. 7, 2008 http://www.youtube.com/watch?v=lqjtTzNEd54&feature=youtu.be%3E [Screenshots retrieved Oct. 23, 2014 in 9 pages].

Martin, C.W., Otto Bock C-leg: A Review of Its Effectiveness, WCB Evidence Based Group, Nov. 27, 2003.

Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.

Proteor, "Assembly and Adjustment Instructions for IP50-R," Sep. 2004, pp. 1-21.

Office Action in Canadian Patent Application No. 2559890, dated Aug. 25, 2011.

Office Action in Canadian Patent Application No. 2559890, dated Jun. 11, 2012.

Office Action in European Patent Application No. 05725431, dated Sep. 23, 2010 in 5 pages.

Official Communication in Canadian Application No. 2595895, dated Aug. 22, 2013.

Official Communication in Canadian Application No. 2595895, dated Apr. 24, 2014.

Official Communication in European Application No. 06748179.6, dated Apr. 4, 2013.

Official Communication in European Application No. 06802543.6, dated Sep. 24, 2013.

Official Communication in European Application No. 06802543.6, dated Jun. 2, 2014.

Extended European Search Report in Application No. 08706182.6, dated Jun. 10, 2011.

Official Communication in European Application No. 08706257.6, dated Nov. 5, 2013.

International Preliminary Report on Patentability in Application No. PCT/IB2012/000998, dated Nov. 14, 2013.

(56) References Cited

OTHER PUBLICATIONS

Abbas, et al., Neural Network Control of Functional Neuromuscular Stimulation Systems: Computer Stimulation Studies, 1995.
Aminian, Kamiar et al., *Estimation of Speed and Incline of Walking Using Neural Network*, IEEE Transactions on Instrumentation and Measurement, vol. 44, No. 3, Jun. 1995, at 743.
Andrews, BIJ., et al., Hybrid FES Orthosis Incorporating Closed Loop Control and Sensory Feedback, *J. Biomed. Eng*. 1988, vol. 10, April, 189-195.
Au, S. K. et al. Powered Ankle-Foot Prosthesis for the Improvement of Amputee Ambulation, Proceedings of the 29th Annual International Conference of the IEEE, Aug. 23-26, 2007.
Bachmann, et al., Inertial and Magnetic Tracking of Limb Segment Orientation for Inserting Humans into Synthetic Environments, 2000.
Bar, A., et al., "Adaptive Microcomputer Control of an Artificial Knee in Level Walking," J. Biomechanical Eng., vol. 5, pp. 145-150, 1983.
Baten, Inertial Sensing in Ambulatory Back Load Estimation, 1996.
Benedetti, Gait Analysis of Patients Affected by Post-Traumatic Ankle Arthrosis Treated with Osteochondral Allograft Transplantation, SIAMOC 2006 Congress Abstracts/Gait & Posture.
Blaya, Force-Controllable Ankle Foot Orthosis (AFO) to Assist Drop Foot Gait, Feb. 2003 (believed to be catalogued on or after Jul. 8, 2003).
Bogert, et al., A Method for Inverse Dynamic Analysis Using Accelerometry, 1995.
Bortz, A New Mathematical Formulation for Strapdown Inertial Navigation, 1971.
Bouten, A Triaxial Accelerometer and Portable Data Processing Unit for the Assessment of Daily Physical Activity, 1997.
Bouten, Carlifin V., et al., Assessment of Energy Expenditure for Physical Activity Using a Triaxial Accelerometer. *Med. Sci. Sports Exerc.*, vol. 26, No. 12, pp. 151-1523, 1994.
Crago, et al., New Control Strategies for Neuroprosthetic Systems, 1996.
Dai R, et al., Application of Tilt Sensors in Functional Electrical Stimulation. IEEE Trans. Rehab. Eng. 1996; 4(2):63-71.
Dietl, H., Der Einsatz von Elektronik bei Prothesen zur Versorgung der unteren Extremitat, Med. Orth. Tech, 1997, vol. 117, pp. 31-35.
Elliott, Scott B., MR Microprocessor-Controlled Swing and Stance, Presentation to American Academy of Orthotists & Prosthetists, Feb. 4, 2004.
Ferrari, A., First in vivo Assessment of "Outwalk", A Novel Protocol for Clinical Gait Analysis Based on Inertial and Magnetic Sensors, Med Biol. Eng. Comput (2010) 48:1-15, published online Nov. 13, 2009.
Fisekovic, et al., New Controller for Functional Electrical Stimulation Systems, 2000.
Foerster, et al., Detection of Posture and Motion by Accelerometry—A Validation Study in Ambulatory Monitoring, 1999.
Foxlin, et al., Miniature 6-DOF Inertial System for Tracking HMDs, 1998.
Frank, K., Reliable Real-Time Recognition of Motion Related Human Activities Using MEMS Inertial Sensors, Asserted by iWalk in Civil Action No. 12-CV-11061 FDS to constitute prior art to U.S. Patent Nos. 7,431,737 and 7,896,927.
Fujita, K. et al., Joint Angle Control with Command Filter for Human Ankle Movement Using Functional Electrical Stimulation, Proceedings of the 9th Annual Conference of the IEEE Engineering in Medicine and Biology Society, Nov. 13-16, 1987.
Gard, Steven A., Ph.D., Use of Quantitative Gait Analysis for the Evaluation of Prosthetic Walking Performance, Journal of Prosthetics & Orthotics, vol. 18, Issue 6, pp. P93-P104, Jan. 2006.
Godha, S., et al., Integrated GPS/INS System for Pedestrian Navigation in a Signal Degraded Environment. ION GNSS 2006, Fort Worth TX, Sep. 26-29, 2006, p. 1-14.
Graps, A., An Introduction to Wavelets, IEEE Computational Science & Engineering, 1995.

Hayes, W.C., et al., Leg Motion Analysis During Gait by Multiaxial Accelerometry: Theoretical Foundations and Preliminary Validations. *Journal of Biomechanical Engineering*, vol. 105, Aug. 1983, p. 283-289.
Heyn, Andreas, et al., The Kinematics of the Swing Phase Obtained From Accelerometer and Gyroscope Measurements, *18th Annual International Conference of the IEEE Engineering in Medicine and Biology Society*, Amsterdan 1996, p. 463-464.
Howard, "Joint and Actuator Design for Enhanced Stability in Robotic Force Control," Ph.D. thesis, Massachusetts Inst. of Technology, Dept. of Aeronautics and Astronautics, 1990.
Jonic, et al., Three Machine Learning Techniques for Automatic Determination of Rules to Control Locomotion, 1999.
Kidder, Steven M., et al., A System for the Analysis of Foot and Ankle Kinematics During Gait. *EEE Transactions on Rehabilitation Engineering*, vol. 4, No. 1, Mar. 1996.
Kirkwood, et al., Automatic Detection of Gait Events: A Case Study Using Inductive Learning Techniques, 1989.
Kooij, et al., A Multisensory Integration Model of Human Stance Control, 1998.
Kostov, et al., Machine Learning in Control of Functional Electrical Stimulation Systems for Locomotion, 1995.
LaFortune, Mario A., Three Dimensional Acceleration of the Tibia During Walking and Running. *J. Biomechanics* vol. 24, No. 10, pp. 877-886, 1991.
Lee, S., Activity and Location Recognition Using Wearable Sensors, Pervasive Computing, IEEE, 2002.
Light, L.H. et al., Skeletal Transients on Heel Strike in Normal Walking with Different Footwear, . Biomechanics, vol. 13, 1980, pp. 477-480.
Luinge, H.J., Inertial Sensing of Movement. Doctoral Thesis, Twente University Press, Enschede, Netherlands (2002) p. 9-13.
Martens, W., *Exploring Information Content and Some Application of Body Mounted Piezo-Resistive Accelerometers*, Phy Vision b.v., Gemert, The Netherlands.
Mayagoitia, Ruth E., et al., Accelerometer and Rate Gyroscope Measurement of Kinematics: An Inexpensive Alternative to Optical Motion Analysis Systems. *Journal of Biomechanics* 35 (2002) 537-542.
McNealy, Lexyne L. and Steven A. Gard, Effect of Prosthetic Ankle Units on the Gait of Persons with Bilateral Trans-Femoral Amputations, Prosthetics and Orthotics International, 2008 32:111.
Moe-Nilssen, A New Method for Evaluating Motor Control in Gait Under Real-Life Environmental Conditions, Parts 1—The instrument; Part 2: Gait Analysis, 1997.
Morris, J.R. W., Accelerometry—A Technique for the Measurement of Human Body Movements, *J. Biomechanis*, 1973, vol. 6, pp. 729-736.
Murray, M. Pat, et al. Walking Patterns of Normal Men, The Journal of Bone and Joint Surgery, vol. 46-A, No. 2, Mar. 1964.
Nakagawa, A., Intelligent Knee Mechanism and the Possibility to Apply the Principle to the Other Joints, Engineering in Medicine and Biology Society, Proceedings of the 20th Annual International Conference of the IEEE, vol. 20, No. 5, Dec. 1998, at 2282.
Otto Bock Orthopadische Industrie, C-Leg A new dimension in amputee mobility, Otto Bock Data Sheet, 1997.
Otto Bock Orthopadische Industrie, The Electronic C-Leg Compact Leg Prosthesis System: Instructions for Use, 2002.
Perry, Jacquelin, MD, Gait Analysis: Normal and Pathological Function, Ch. 4, pp. 51-53, 85-87, 1992.
Petrofsky, Jerrold S., et. al., Feedback Control System for Walking in Man. *Comput. Biol. Med*. vol. 14, No. 2, pp. 135-149, 1984.
Popovic, Dejan et al., Control Aspects of Active Above-Knee Prosthesis, International Journal of Man-Machine Studies, vol. 35, Issue 6, Dec. 1991, at 751.
Raggi, M., et al. Wearable Sensors for the Real-Time Assessment of Gait Temporal Symmetry in Above-Knee Amputees: The 'SEAG' Protocol, Abstracts of the 2007 SIAMOC Congress.
Raggi, M., et al., Gait Analysis Through Inertial Sensors in Transfemoral Amputees: Step and Stride Regularity, SIAMOC 2006 Congress Abstracts/Gait & Posture.

(56) References Cited

OTHER PUBLICATIONS

Reitman, J. S., et al., Gait Analysis in Prosthetics: Opinions, Ideas, and Conclusions, Prosthetics and Orthotics International, 2002, 26, 50-57.

Robinson, David W. et al., *Series Elastic Actuator Development for a Biomimetic Walking Robot*, MIT Leg Laboratory, 1999.

Robinson, David William, *Design and Analysis of Series Elasticity in Closed-Loop Actuator Force Control*, MIT Department of Mechanical Engineering, Jun. 1996.

Sekine, et al., Classification of Waist-Acceleration Signals in a Continuous Walking Record, 2000.

Sin S. W., et al., Significance of Non-Level Walking on Transtibial Prosthesis Fitting with Particular Reference to the Effects of Anterior-Posterior Alignment, Journal of Rehabilitation Research and Development vol. 38 No. 1, Jan./Feb. 2001, p. 1-6.

Smidt, G.L., et al., An Automated Accelerometry System for Gait Analysis, *J. Biomechanics*. 1977, vol. 10, pp. 367-375.

Su, P-F, et al., The Effects of Increased Prosthetic Ankle Motions on the Gait of Persons with Bilateral Transtibial Amputations, Am. J. Phys. Med. Rehabil., vol. 89, No. 1, Jan. 2010.

Tomovic, R. et al., *A Finite State Approach to the Synthesis of Bioengineering Control Systems*, IEEE Transactions on Human Factors in Electronics, vol. HFE-7, No. 2, Jun. 1966.

Tong, et al., Virtual Artificial Sensor Technique for Functional Electrical Stimulation, 1998.

Tong, Kaiyu and Malcolm H. Granat, *A Practical Gait Analysis System Using Gyroscopes*, Medical Engineering & Physics, vol. 21, No. 2, Mar. 1999, at 87-94.

U.S. Appl. No. 60/371,974 to Martin, filed Apr. 12, 2002.

Veltink, et al., Detection of Static and Dynamic Activities Using Uniaxial Accelerometers, 1996.

Veltink, Peter H. et al. (1993), The Feasibility of Posture and Movement Detection by Accelerometry, in 15th Annual International Conference of the IEEE Engineering in Medicine and Biology Society, Oct. 28-31, 1993, San Diego, CA, 1230-1231.

Willemsen, A. TH. M., et al., Real-Time Gait Assessment Utilizing a New Way of Accelerometry. *J. Biomechanics* vol. 23, No. 8, pp. 859-863, 1990.

Willemsen, Antoon Th. M., et al., Automatic Stance-Swing Phase Detection from Accelerometer Data for Peroneal Nerve Stimulation. *IEEE Trasnactions on Biomedical Engineering*, vol. 37, No. 12, Dec. 1990, p. 1201-1208.

Williamson, Matthew M., *Series Elastic Actuators*, Massachusetts Institute of Technology Artificial Intelligence Laboratory, A.I. Technical Report No. 1524, Jan. 1995.

Woodward, M I, et al., Skeletal Accelerations Measured During Different Exercises. *Proceedings of the Institution of Mechanical Engineers*, Part H: Journal of Engineering Medicine 1993 207:79, DOI: 10.1243/PIME_PROC_1993_207_274_02.

Wu Ge, The Study of Kinematic Transients in Locomotion Using the Integrated Kinematic Sensor, IEEE Transactions on Rehabilitation Engineering, vol. 4, No. 3, Sep. 1996, p. 193-200.

"MT9 Inertial 3D Motion Tracker," Xsens Technologies B.V., available at http://www.xsens.com/download/MT9_brochure.pdf (at least as early as Oct. 2004), printed Jul. 20, 2006.

Au, et al., "An EMG-Position Controlled System for an Active Ankle-Foot Prosthesis: An Initial Experimental Study" Rehabilitation Robotics, 2005, ICORR 2005., 9th International Conference in Chicago, IL, Jun. 28-Jul. 1, 2005, Piscataway, NJ, IEEE, Jun. 28, 2005, pp. 375-379, XP008078417.

Australian Office Action dated Apr. 6, 2010 in Patent application No. 2005215769, filed Feb. 11, 2005, Apr. 6, 2010.

Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1; pp. 24-31, Mar. 2004.

Blumentritt, Siegmar, Ph.D., et al., Design Principles, Biomedical Data and Clinical Experience With a Polycentric Knee Offering Controlled Stance Phase Knee Flexion: A Preliminary Report, Journal of Prothetics and Orthotics, 1997, vol. 1, Issue 9, pp. 18-24.

Flowers, et al., Journal of Biomechanical Engineering: Transactions of the ASME; Feb. 1977, pp. 3-8.

Herr, et al., "User-adaptive control of a magnetorheological prosthetic knee", Industrial Robot: an International Journal, vol. 30, No. 1, (2003) pp. 42-55.

Kirsner, Scott, A Step in the Right Direction Biomedical Horizons Expanding, Boston Globe, Mar. 17, 2003.

Lelas, et al., Hydraulic versus Magnetorheological-based Electronic Knee Protheses: A Clinical Comparison, Harvard Medical School, Dept. of Phys. Med. and Rehab., Boston, MA, pp. 16—Jan.

Otto Bock Orthopadische Industrie, The Electronic C-Leg Knee Joint System: Instructions for Use, available at http://www.ottobockus.com/products/lower_limb_prosthetics/c-leg_instructions.pdf, 32 pages (printed Jul. 20, 2006).

Popovik, D., et al., Optimal Control for an Above-Knee Prosthesis With Two Degrees of Freedom, J. Biomechanics, 1995, vol. 1, Issue 28, pp. 89-98.

State-of-the Art Prosthetic Leg Incorporates Magneto-Rheological Technology, Medical Product Manufacturing News, Nov. 2000, pp. 42.

Suga, T., et al., "Newly designed computer controlled knee-ankle-foot orthosis (Intelligent Orthosis)", Prosthetics and Orthotics International, 1998, 22, 230-239.

Thakkar, Sneha, Energy Economy Gait Analysis of an Autoadaptive Prosthetic Knee, Master's Thesis submitted to the Dept. of Electrical Engineering and Computer Science, MIT, Dept. of Electrical Engineering and Computer Science, MIT, 2002, pp. 1-58.

Townsend M A et al., "Biomechanics and modeling of bipedal climbing and descending." Journal of Biomechanics 1976, vol. 9, No. 4, pp. 227-239, XP008078405.

Van Der Loos, H.F.M., et al, ProVAR Assistive Robot System Architecture, Proceedings of the 1999 IEEE International Conference on Robotics & Automation; Detroit, Michigan, May 1999.

Wilkenfeld, Ari Ph.D., et al., An Auto-Adaptive External Knee Prosthesis, Artificial Intelligence Laboratory, MIT, Cambridge, Massachusetts, Sep. 2000, pp. 3.

Wilkenfeld, Ari, Ph.D., Biologically inspired autoadaptive control of a knee prosthesis, Dissertation Abstract, MIT, Cambridge, Massachusetts, Sep. 2000, pp. 1.

\* cited by examiner

IMPEDANCE SIMULATING MOTION CONTROLLER FOR ORTHOTIC AND PROSTHETIC APPLICATIONS

TECHNICAL FIELD

The present invention relates to an impedance simulating motion controller for orthotic and prosthetic applications.

BACKGROUND

Prosthetic and/or orthotic devices ("PODS") for restoring or replacing lost lower-limb functions have been available for many years. Until recently, both types of devices were found as purely mechanical linkages making advantageous usage of simple mechanisms in order to preclude knee buckling in level walking stance phase, while still ensuring some form of swing motion during the aerial phase. While this type of device was shown to be fairly efficient in restoring the structural aspects of the lower-limb role in gait, their incapacity to properly sustain the wide variety of lower-limb dynamics associated with the various gait locomotion activities performed on a daily basis appeared as a sufficient limitation to sustain the development of more advanced devices.

While significant efforts have been directed towards designing more advanced mechanisms allowing easier adjustment, or more progressive action, through pneumatics and hydraulics, the rapid advances in energy storage and computer technologies soon allowed to extend the realm of capacities associated with typical PODS. Real-time configuration of passive braking devices such as disclosed, for example, in U.S. Pat. No. 5,383,939 and US Patent Application Publication No. 2006/0136072 A1, greatly improved the adaptability of PODS to user gait specificities or to variations of the environment in which the locomotion tasks are performed. Moreover, these PODS allowed the addressing of energy dissipative locomotion tasks in a physiologically-compliant manner never seen before. Although showing increased performance and dynamic adaptation with respect to the locomotion tasks being undertaken when compared to their predecessors, this first generation of computer-controlled PODS still lacked the adaptability and flexibility required to smoothly integrate into users' daily lives.

Integration of computer controls to PODS brought about the necessity for some sort of control system in order to link sensory inputs to the now dynamically configurable actuator. However, the purely dissipative nature of these devices greatly simplifies the problem as mechanical power exchanges between the user and the device are unidirectional (i.e., user has to initiate all tasks and provide mechanical power).

Latest efforts in the field of advanced PODS, such as disclosed, for example, in U.S. Patent Application Publication No. 2004/0181289 A1, herein incorporated by reference in its entirety, partly resolved some of the limitations observed in the first generation of computer-controlled PODS by providing a fully motorized prosthetic platform, allowing to address all major locomotion tasks, irrespective of their generative or dissipative nature. Requirements for computer-controlled system appeared quite more complex as the interactions between the user and the prosthetic or orthotic device were no longer solely initiated by the user himself. Through the use of a two layer control system, the motorized prosthetic and/or orthotic device ("POD") was allowed to efficiently manage the mechanical power exchange between the user and the device, such that the synergy between user and motorized POD globally benefited the user. Adequate usage of the POD capacity to generate mechanical power was observed to lead to increased gait quality and activity levels.

Nevertheless, the use of strict state machines to implement the artificial intelligence engine as the highest layer of the POD control system is observed to impose a certain formalism on the manner in which the user executes typical locomotion tasks. While generating a certain learning burden on the user side, the use of firm triggers in order to trigger either distinct state transition or specific joint behavior greatly affects man-machine symbiosis. Moreover, limitations associated with the use of a strict state machine artificial intelligence engine when working in a highly variable environment (i.e., external environment and user himself) are well known and quickly show up as robustness issues from a system perspective. Finally, processing associated with the extraction of complex features associated with specific locomotion task detection is also known to generate a latency between measurement of the sensors value and implementation of the actual actions, which is often observed to greatly affect the POD usability and performance.

Furthermore, common PODS lack the ability to properly reproduce natural knee joint behavior and dynamic properties when used in a context that significantly differs from typical locomotion tasks. While generation of proper joint dynamics during cyclical locomotion portions ensure high symbiosis and user benefits, limitations observed in the capacity to reproduce natural joint compliance, or motions, in either non-locomotor or non-cyclical tasks significantly affect POD usability and, accordingly, associated user benefits.

Based on these last observations, it clearly appears that requirements for an improved orthotic and prosthetic control system exist. More specifically, a need to develop a control system architecture and associated engines that are able to sustain more efficiently limited ambulation, as well as non-cyclical and cyclical gait for users suffering of either amputation of the lower-limb or dysfunction requiring the use of an orthosis or prosthesis exists.

SUMMARY

In accordance with the present disclosure there is provided a controller for controlling a motorized prosthetic or orthotic device provided with a joint. In one embodiment, the controller includes an equilibrium trajectory generator configured to receive locomotion data regarding the locomotion of a user of a motorized prosthetic or orthotic device, and generate one or more control parameters to control the motorized prosthetic or orthotic device based at least on the locomotion data, a dynamic trajectory compensator configured to dynamically to generate one or more compensated control parameters by adjusting at least one control parameter from the one or more control parameters based at least on one physiological characteristic of the user, a dynamic gain tuner configured to generate one or more tuned control parameters by dynamically modifying at least one of the one or more compensated control parameters using a gain scaling factor, and a proportional-derivative position controller configured to generate one or more control signals using the one or more tuned control parameters, wherein the control signals are used to control movement of an actuator.

In one embodiment, the locomotion data includes at least locomotion portion data and phase of locomotion data, and the equilibrium trajectory generator receives the locomotion data from a locomotion recognition module. In one embodiment, the equilibrium trajectory generator calculates one or more control parameters based on general characteristics of human locomotion using non-complex mathematical relationships. In one embodiment, the equilibrium trajectory generator generates the one or more control parameters based on an equilibrium trajectory. In one embodiment, the one or more control parameters comprise at least one of a desired position, a proportional gain, and a derivative gain. In one embodiment, the dynamic trajectory compensator is further configured to dynamically compensate the at least one control parameter based at least on one of dynamic stiffness, joint expected loading, and desired kinematic behavior. In one embodiment, at least one physiological characteristic is at least one of body mass and weight. In yet another embodiment, the dynamic gain tuner calculates the gain scaling factor using at least one of a measured deflection value at a first time, an expected deflection value at the first time, and an equilibrium value at the first time. In one embodiment, the first time is the time at which the controller measures the maximal deflection value from the equilibrium trajectory during the stance phase of the gait cycle.

The description further includes a method of controlling a motorized prosthetic or orthotic device provided with a joint. In one embodiment, the method includes receiving locomotion data regarding the locomotion of a user of a motorized prosthetic or orthotic device, generating one or more control parameters to control the motorized prosthetic or orthotic device based at least on the locomotion data, dynamically adjusting at least one of the one or more control parameters based at least on one physiological characteristic of the user, and generating one or more control signals using at least the dynamically adjusted control parameter to control movement of an actuator.

In one embodiment, the method can further include determining whether a difference between a measured deflection value and an expected deflection value falls within a tolerance level, and modifying the at least one adjusted control parameter when it is determined that the difference between the measured deflection value and the expected deflection value falls outside the tolerance level.

The description further includes a motorized prosthetic or orthotic device. In one embodiment, the motorized prosthetic or orthotic device includes a proximal segment, a distal segment, a joint segment coupling the proximal segment to the distal segment, an actuator coupled to the distal segment and configured to actuate the distal segment with respect to the proximal segment, and a controller configured to generate one or more control parameters based on locomotion data of a user and at least one physiological characteristic of the user, generate one or more tuned control parameters by dynamically modifying at least one of the one or more control parameters using a gain scaling factor, and transmit control signals to the actuator based on the one or more tuned control parameters.

The description further includes a method of controlling a motorized prosthetic or orthotic device provided with a joint. In one embodiment, the method includes receiving locomotion data regarding the locomotion of a user of a motorized prosthetic or orthotic device, generating one or more control parameters to control one or more actuators of the motorized prosthetic or orthotic device based at least on the locomotion data and an equilibrium trajectory, wherein the equilibrium trajectory is calculated using kinematic data, generating one or more control signals for the one or more actuators based on the one or more control parameters, and transmitting the one or more control signals to the actuator.

In one embodiment, the equilibrium trajectory is calculated using a regression line of torque-angle during a stance phase of a gait cycle. In another embodiment, the equilibrium trajectory is different from normal knee joint kinematic behavior. In yet another embodiment, the kinematic data is Winter's kinematic data. In one embodiment the method uses the equilibrium trajectory to approximate a kinematic reference model. In one embodiment, the kinematic reference model is Winter's Reference Trajectory.

In one embodiment the method further includes generating control signals using a proportional-derivative controller and the control parameters to control actuation of the actuator, wherein the control signals set a stiffness value for the actuator such that knee angle deflection of the motorized prosthetic or orthotic device approximates a kinematic reference model. In one embodiment, the one or more control parameters include at least a position set-point, a proportional gain, and a derivative gain. In one embodiment, the equilibrium trajectory is approximately constant during at least a portion of the stance phase of a gait cycle.

BRIEF DESCRIPTION OF THE FIGURES

Embodiments of the invention will be described by way of example only with reference to the accompanying drawings, in which.

DETAILED DESCRIPTION

Generally stated, the non-limitative illustrative embodiment of the present invention provides an impedance simulating motion controller for prosthetic and/or orthotic devices ("PODS") for restoring lost locomotor functions, or facilitate gait re-education resulting from various pathologies. The impedance simulating motion controller is a low-level motion controller that makes use of a position controller formulation combined with the implementation of specific knee joint compliance such that the position tracking constraint of the controller is relaxed to allow behavior similar to what can be observed on the human knee joint. To this end, instead of adopting the usual position control strategy consisting of enforcing a very stiff position tracking of the time-based position trajectory, the impedance simulating motion controller implements a loose position tracking strategy, where the deviation between a reference (equilibrium) trajectory and actuator motion is calibrated in such a way as to simulate the human knee joint natural behavior and mechanical impedance. The impedance observed at the knee joint can also be referred to as stiffness, or dynamic stiffness.

Figure 1:
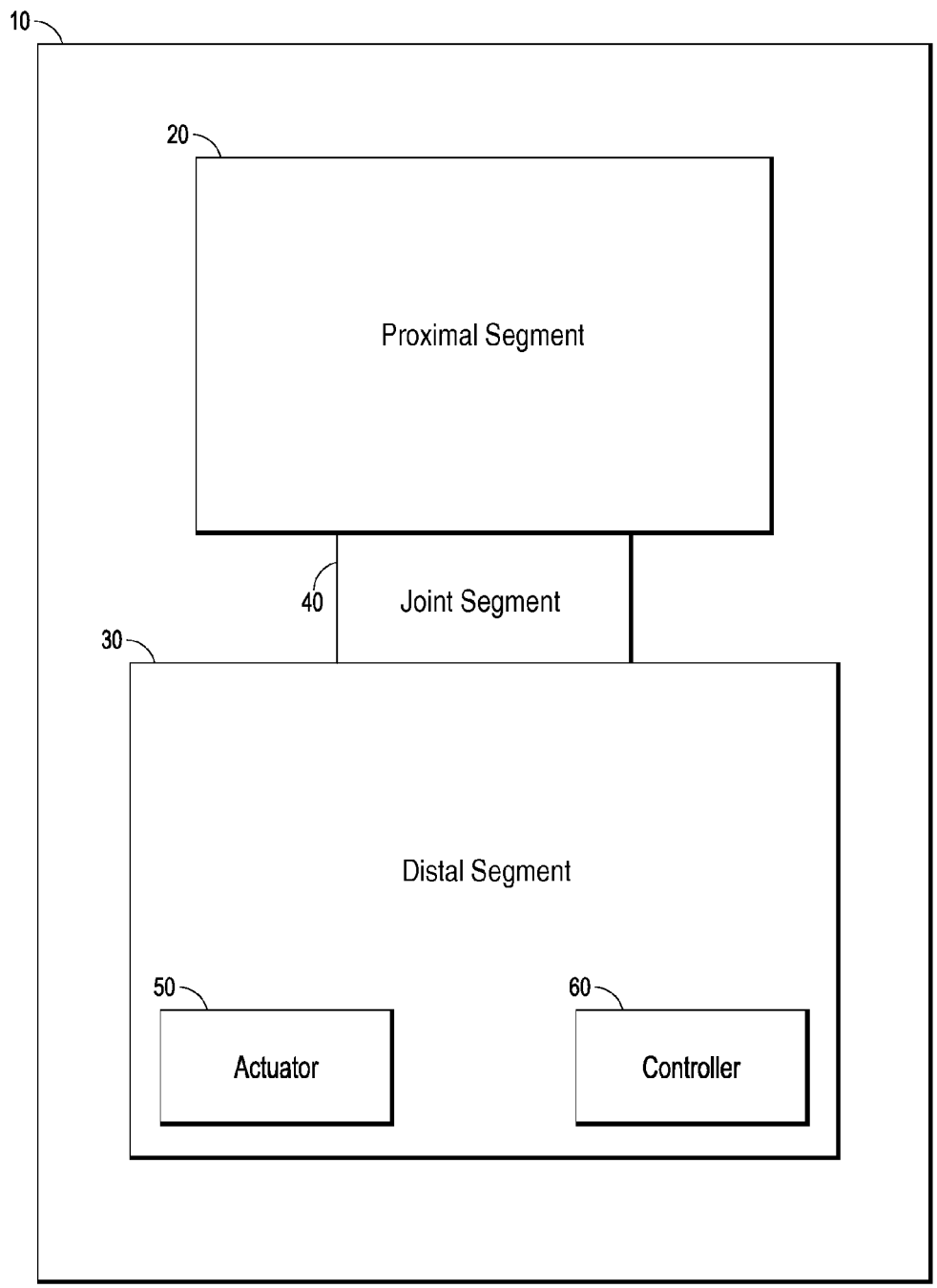
FIG. 1 is a block diagram of a motorized prosthetic and/or orthotic device ("POD")

FIG. 1 illustrates a block diagram of a motorized prosthetic and/or orthotic device ("POD") 10, which includes a proximal segment 20, a distal segment 30, a joint segment 40, an actuator 50, and a controller 60. Examples of such PODS are discussed in greater detail, with reference to U.S. Pat. No. 7,867,284, entitled CONTROL SYSTEM AND METHOD FOR CONTROLLING AN ACTUATED PROSTHESIS; U.S. Pat. No. 7,137,998, entitled POSITIONING OF LOWER EXTREMITIES ARTIFICIAL PROPRIOCEPTORS; and U.S. Pat. No. 7,815,689, entitled, INSTRUMENTED PROSTHETIC FOOT; and U.S. Publication Nos. 2009-0299480, entitled JOINT ACTUATION MECHANISM FOR A PROSTHETIC AND/OR ORTHOTIC DEVICE HAVING A COMPLIANT TRANSMISSION; and 2010-0160844, entitled HIGH TORQUE ACTIVE MECHANISM FOR ORTHOTIC AND/OR PROSTHETIC DEVICES; all of which are herein incorporated by reference in their entirety.

The proximal segment 20 can include a socket to hold the stump of an amputee. Furthermore, the proximal segment 20 can be connected to the distal segment 30 via the joint segment 40. In one embodiment, the distal segment 30 includes the actuator 50. In other embodiments the actuator can be located between the proximal segment 20 and the distal segment 30. The actuator can be implemented using a screw actuator, however, other types actuators may be used without departing from the spirit and scope of the description. The controller 60 can be located in any number of locations, including the proximal segment 20, the distal segment 30, or the joint segment 40. The controller 60 can be an impedance simulating motion controller, which will be described in greater detail below, with reference to the remaining figures.

Figure 2A:
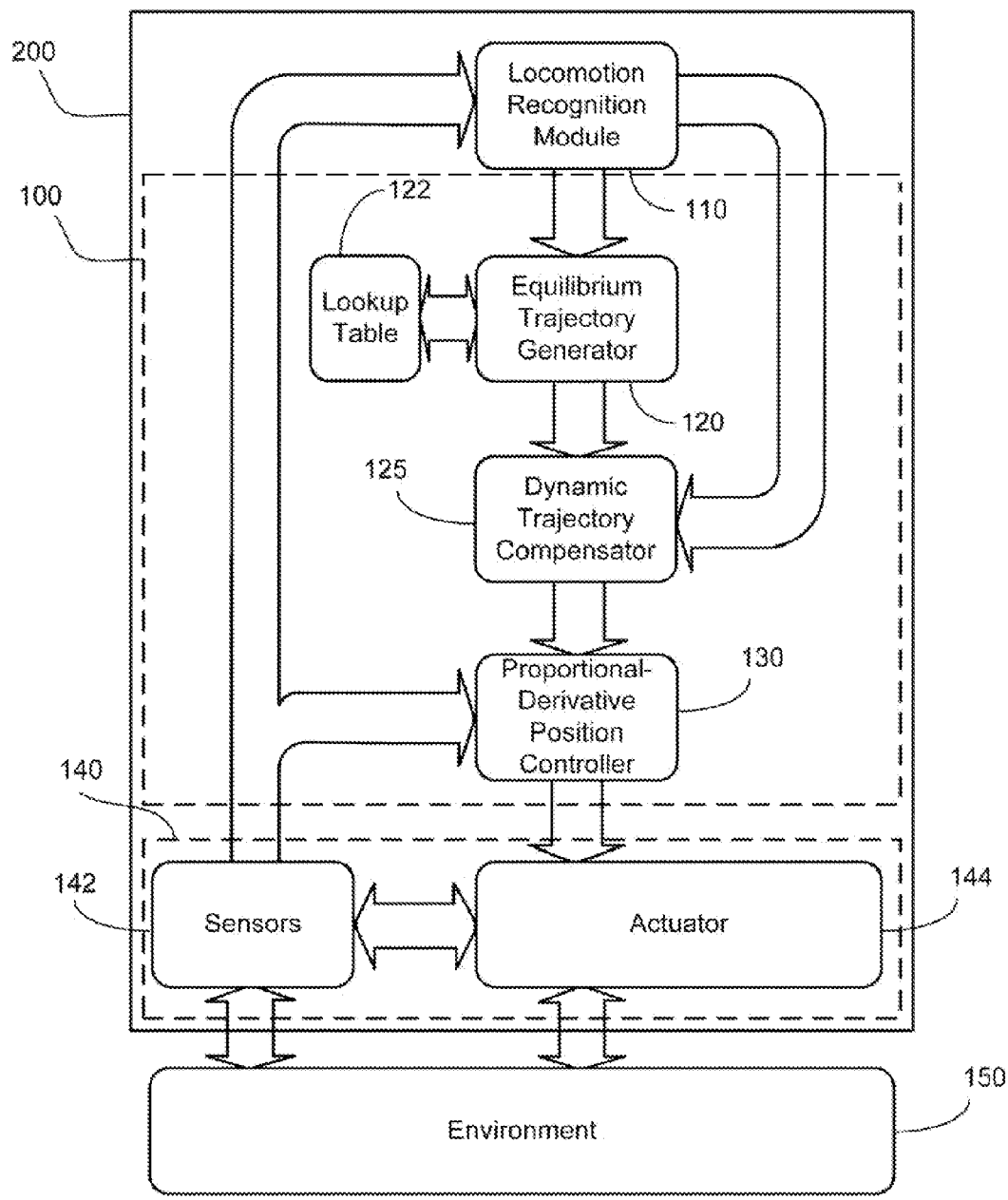
FIG. 2A is a block diagram of a motorized POD which comprises an impedance simulating motion controller.

Referring to FIG. 2A, there is shown a block diagram of a motorized prosthetic and/or orthotic device ("POD") 200 which comprises a locomotion recognition module 110, an impedance simulating motion controller 100, sensors 142, and one or more actuators 144. Examples of motorized knee prostheses are shown in U.S. Pat. No. 7,314,490 entitled "ACTUATED LEG PROSTHESIS FOR ABOVE-KNEE AMPUTEES", U.S. Patent Application Publication No. 2004/0181289 entitled "ACTUATED PROSTHESIS FOR AMPUTEES" and U.S. Patent Application Publication No. 2006/0122711 A1 entitled "ACTUATED LEG PROSTHESIS FOR ABOVE-KNEE AMPUTEES", all by Bedard, all of which are incorporated by reference herein in their entirety.

The sensors 142 and one or more actuators 144 interact with the environment and can provide information to the motorized POD 200 regarding location, speed, and other information about the POD 200 to the impedance simulating motion controller 100. For example, the sensors 142 may be in the form of one or more position encoders providing an angle of a corresponding joint of the motorized POD 200. The one or actuators 144, controlled by the impedance simulating motion controller 100, generate behavior to sustain a predefined kinematics behavior with the environment 150. The one or more actuators 144 can be implemented using any number of different actuator types. In one embodiment, the one or more actuators are linear actuators.

The impedance simulating motion controller 100 includes an equilibrium trajectory generator 120 with an associated lookup table 122, a dynamic trajectory compensator 125 and a proportional-derivative position controller 130, and is used in association with a locomotion recognition module 110.

An example of a locomotion recognition module 110, a trajectory generator 120, and associated lookup table 122 is described in U.S. Patent Application Publication No. 2006/0122710 A1 entitled "CONTROL DEVICE AND SYSTEM FOR CONTROLLING AN ACTUATED PROSTHESIS" by Bedard, herein incorporated by reference in its entirety.

The locomotion recognition module 110 gathers data provided by the sensors 142 to calculate information about the user's locomotion (e.g. level walking, stairs ascent, stairs descent, etc.). The locomotion information can be further subdivided into a locomotion portion and phases of locomotion portion. In one embodiment, the locomotion information is provided to the equilibrium trajectory generator 120. In other embodiments, the locomotion data is provided directly to a dynamic gain tuner, described in greater detail below with reference to FIGS. 14, 15, and 16.

The equilibrium trajectory generator 120 uses the locomotion data received from the locomotion recognition module 110, to generate control parameters to control the actuator 144. The control parameters are calculated based on general characteristics of human locomotion as well as the locomotion data. Thus, based on the cadence, type of movement (level walking, stair ascent/descent, incline, decline, etc.), stride length, etc., the equilibrium trajectory module can select the appropriate control parameters. The general characteristics human locomotion can be obtained using kinematic and kinetic data generated by observing human gait cycles. In one embodiment, the data used is Winter's kinematics and kinetic data as described in *The Biomechanics and Motor Control of Human Gait*, Winter, D. A., University of Waterloo, 72 p., Waterloo, 1987. Throughout the specification reference is made to Winter and Winter's data. However, it is to be understood that other kinematics data can be used to implement the features described herein without departing from the spirit and scope of the description.

The control parameters can be generated using non-complex mathematical relationships whose coefficient values are stored in the lookup table 122. These mathematical relationships (time-dependant equations and static characteristics) characterize the relationships between the locomotion of the user and the control parameters. Furthermore, the kinematic data that describes the general characteristics of human gait, mentioned above, can be used to create an equilibrium trajectory, described in greater detail below with reference to FIGS. 4A-12. Based on the equilibrium trajectory, the appropriate coefficient values for the control parameters can be selected. The control parameters generated by the equilibrium trajectory generator 120 include, but are not limited to, desired position $\Theta_d$ set-points, and proportional gain $K_P$, and derivative $K_D$ gain. As mentioned previously, the control parameters can be used by the proportional-derivative position controller 130 to generate the control signals to control the actuator 144. It is to be understood that additional, or different, information may also be used, such as speed.

The equilibrium trajectory generator 120 and dynamic trajectory compensator 125 are configured to generate the control parameters for the actuator 144 so that the POD 200 approximates a desired kinematic behavior or a kinematic reference model. The kinematic reference model can be based on Winter's Reference Trajectory. In one embodiment, the equilibrium trajectory generator 120 with its associated lookup table 122 and the proportional-derivative (PD) controller 130 forms the motion controller, while the dynamic trajectory compensator 125 defines the loose position tracking strategy that simulates impedance motion control. In this embodiment, the equilibrium trajectory generator 120 outputs the control parameters without regard to the physiological characteristics of the user. The dynamic trajectory compensator 125 then compensates the control parameters based on physiological characteristics of the user. In this way, the POD 200 kinematics can more closely model normal kinematic behavior. The equilibrium trajectory and stiffness can be set such that the kinematic behavior of the POD 200 approximates a desired kinematic behavior or kinematic reference model, such as Winter's Reference Trajectory.

Figure 2B:
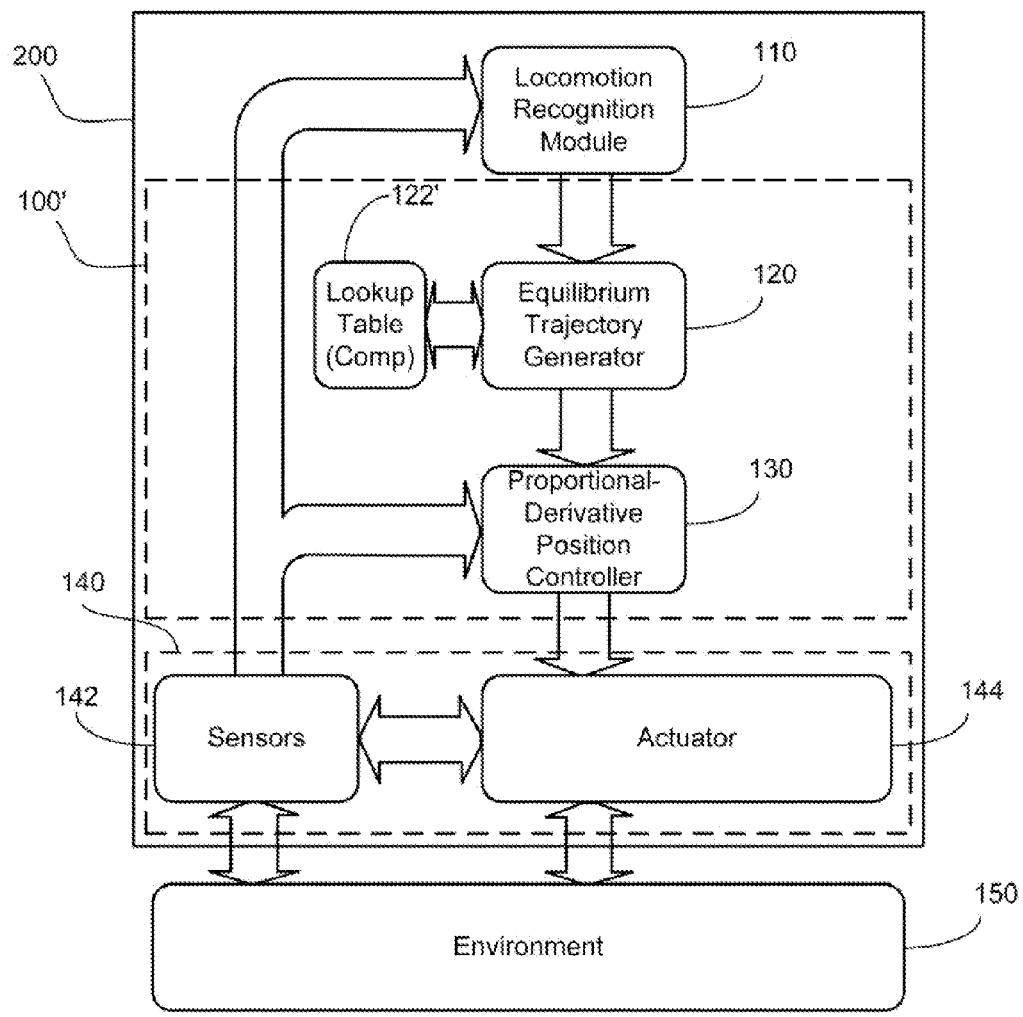
FIG. 2B is a block diagram of a motorized POD which comprises an impedance simulating motion controller according to an alternative embodiment.

In an alternative embodiment, illustrated in FIG. 2B, the lookup table 122', associated with the equilibrium trajectory generator 120, can be modified to contain values that have already been compensated at manufacturing for user physiological characteristics. In this manner, the controller 100' can provide a simulated impedance motion control capability without the dynamic trajectory compensator 125. In other words, the lookup table 122' in controller can contain the compensated values, or compensated control parameters, before the user begins a gait cycle. Rather than dynamically compensating for the physiological characteristics of the user during, or between, gait cycles, the controller 100' can already have the compensated values stored. The calibration that occurs to obtain the compensated values based on the physiological characteristics of the user is referred to below as the static calibration model. Alternatively, as mentioned, the dynamic trajectory compensator 125 can adjust the control parameters dynamically. This can occur in real-time, during user walking, or movement, and can occur during or between gait cycles.

Both impedance simulating motion controllers 100 and 100' will be described in greater detail below.

Position Control

The proportional-derivative position controller 130 uses the control parameters compensated by the dynamic trajectory compensator 125 (or directly from the equilibrium trajectory generator 120 in the case of the impedance simulating motion controller 100' of FIG. 2B) and feedback signals from the sensors 142 to adjust the control signals that the impedance simulating motion controller 100 (or 100') provides to the actuator 144.

Figure 3:
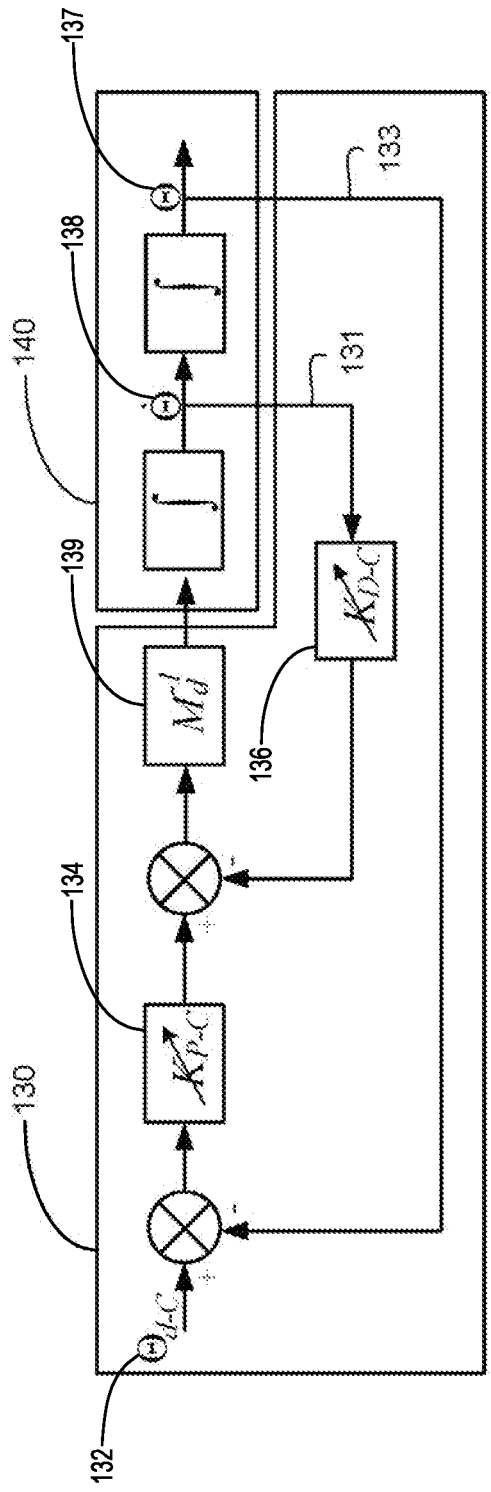
FIG. 3 is a schematic representation of the proportional-derivative position controller and the motorized POD, which is represented by the Laplace-domain double integrator.

Referring to FIG. 3, there is shown a schematic representation of the proportional-derivative position controller 130 and the motorized POD 200, which is represented by the Laplace-domain double integrator. Position $\Theta$ and velocity $\dot{\Theta}$ feedback loops 133 and 131, respectively, are closed to form a tracking controller where the position $\Theta_{d-C}$ set-point 132 is used as a comparison value. Furthermore, variable gains $K_{P-D}$ 134 and $K_{D-C}$ 136 are applied to both measured position $\Theta$ 137 and velocity $\dot{\Theta}$ 138 feedback values.

Finally the mass gain $M_d^{-1}$ 139 affects the actuator 144 force set-point allowing the simulation of system apparent inertia through appropriate scaling of proportional-derivative position controller 130 output.

In FIG. 3, $\Theta_{d-C}$ 132, $K_{P-C}$ 134 and $K_{D-C}$ 136 represent the control parameters compensated either dynamically by the dynamic trajectory compensator 125 or at manufacturing in the compensated lookup table 122'.

Dynamic Trajectory Compensator

The dynamic trajectory compensator 125 dynamically adjusts the control parameters generated by the equilibrium trajectory generator 120, to generate compensated control parameters. Specifically, the dynamic trajectory compensator 125 can dynamically adjust the desired position $\Theta_d$ set-points, proportional gain $K_P$, and derivative $K_D$ gain, with respect to the locomotion task being undertaken by the motorized POD 200 and the physiological characteristics of the user to generate the compensated control parameters. In this manner, the dynamic trajectory compensator 125 can facilitate natural interactions and dynamics between the user and the motorized POD 200.

The dynamic trajectory compensator 125 can use different techniques to generate the compensated control parameters based on the control parameter being adjusted. To determine the compensated position set-point $\Theta_{d-C}$ 132, the dynamic trajectory compensator 125 can use knee dynamic stiffness data (e.g. FIGS. 5, 8, 11), knee joint expected loading (e.g. user physiological characteristics), and a kinematics reference model or desired kinematics behavior (e.g. Winter's Reference Trajectory). As for the determination of the compensated variable gains $K_{P-C}$ and $K_{D-C}$, the dynamic trajectory compensator 125 can use a static calibration model, which allows the automatic definition of proportional-derivative position controller 130 gains based on user physiological characteristics.

Knee Joint Physiological Stiffness Computation

The static calibration model used for determining the compensated variable gains $K_{P-C}$ 134 and $K_{D-C}$ 136 is based on results obtained from the analysis of knee joint torque-angle cyclograms of normal subjects performing various locomotion tasks, e.g. level walking, stairs ascent, stairs descent, etc and specific user physiological characteristics. In one embodiment, the user physiological characteristic used is user body mass (including the motorized POD 200), which is known to affect the knee joint dynamic behavior. The static calibration model is based on the estimated normal knee joint stiffness as found for natural cadence level walking.

The static calibration model is developed based on Winter's kinematics and kinetic data as described above. However, it is to be understood that other kinematics data can be used to implement the features described herein without departing from the spirit and scope of the description. The use of body mass normalized knee joint torque values to define the static calibration model provides body mass dependency in the model. While the static calibration model described uses the natural cadence level walking estimated joint stiffness, stairs ascent and descent cases are also analyzed in order to quantify the joint impedance specifications for these specific portions.

In one embodiment, the physiological characteristic used to describe the knee joint behavior during typical locomotion tasks is the body mass. Body mass, for both amputees and non-amputees, directly affects the actual lower-limb articulation behavior under loading. Modifying the body mass directly modifies the level of loading observed at the articulation, similar to the effects of a payload, and leads to a modification of the knee joint dynamic stiffness in order to reduce its effects on the position response. Other generally lower-limbs normalization schemes (i.e., body weight, body weight times height) can also be used. Furthermore, other physiological characteristics can be used, such as BMI, stride length, segment length, shank to thigh length ratio, knee load, body center of mass, or other parameters that would aid in describing how force is transmitted to the knee by the body mass.

Knee Joint Torque-Angle Diagram Analysis

Figure 5:
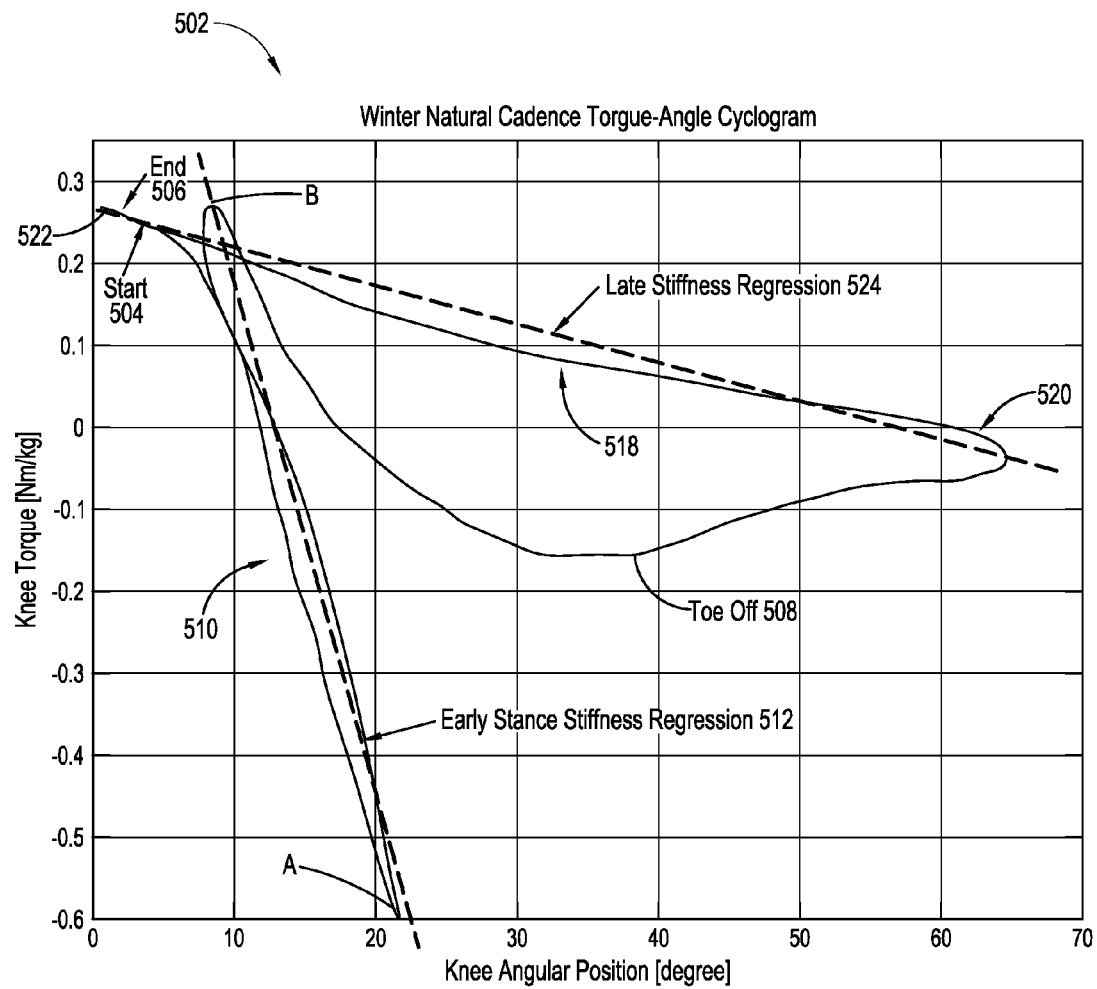
FIG. 5 is a level walking cyclogram based on Winter's data.

Referring to FIG. 5, which provides an example of a torque-angle cyclogram 502 generated from Winter's data for normal gait cadence, the cyclogram starts at heel strike, labeled "start" 504 and circulates towards the point labeled "End" 506, which corresponds to the last point of the gait cycle. Using Winter's convention, toe-off 508 occurs at approximately 60% of the gait cycle and marks lower-limb system configuration transition from an interacting state to a non-interacting state.

From FIG. 5, it can be observed that the torque-angle characteristic presents at least two regions where the curve can generally be approximated by a straight line. The first region 510 includes a clockwise loop in the stance phase of the gait cycle. In this region of the cyclogram 502, a straight line 512 that stretches between the minimal torque position, point A, and the maximal torque position, point B, can approximate the first region 510 of the curve. As the region 510 more or less corresponds to the loading part of the stance and the slope of the regression line 512 of the torque-angle characteristic is fairly constant, the knee joint dynamic stiffness can be approximated by a constant throughout the stance phase of the gait for level walking. The regression line 512 can further be used to calculate the equilibrium trajectory. Non-linear behavior of the torque-angle curve where imputed to hysteresis can be caused by viscous friction and joint internal damping.

The second region displaying a fairly linear behavior of the torque-angle characteristic 518 is found at the late swing phase and stretches between the maximal angle point 520 and the minimal angle point 522. The second region 518 of the gait cycle includes the knee joint extension motion used to bring back the lower-limb in its pre-heel strike configuration. Again, the slope of the linear trend regression line 524 during a stance phase of the torque-angle curve represents the dynamic stiffness of the knee joint for that specific part of the gait cycle and these particular conditions, and can be used to calculate the equilibrium trajectory.

Between the two linear regions 510, 518, the torque-angle curve presents a fairly non-linear behavior. The lower-limb configuration transition phase found between the early stance and the late swing can be characterized by an important variation of the knee joint dynamic stiffness, which generates the non-linear behavior of the torque-angle characteristic.

The late swing region of the characteristic curve displays a lower stiffness value than what is observed for the early stance phase. The swing phase stiffness can therefore be accounted for as being a scale down of the stance phase.

Level Walking Torque-Angle Diagram

As previously mentioned, the stiffness estimated during the early stance phase of the gait cycle using Winter's angle and torque data for normal gait cadence can provide satisfactory baseline controller gains, i.e. $K_{P-C}$ and $K_{D-C}$. Moreover, as discussed earlier, the dynamic stiffness, or impedance, characterizing the knee joint during typical level gait activities can be estimated from the slope of the torque-angle stance-phase linear regression line. The static calibration model can be calculated using the least-square regression of the selected torque-angle characteristic points to the linear template, similar to the equilibrium trajectory. In addition, the static calibration model can be based on user specific physiological characteristics so that the observed knee deflection closely follows a predefined kinematic reference model, such as the Winter Reference Trajectory.

With continued reference to FIG. 5, there is shown the early stance and late swing phase linear regression lines 512, 524 superposed onto the Winter's torque-angle data. It can be observed that the stiffness displayed by the knee joint during the stance phase is quite different from the one displayed during the swing phase. This difference can be explained by the different lower-limb mechanical configuration characterizing each phase of the gait cycle, as well as the difference in torque perturbations amplitude at the knee joint.

Table 1 provides the numerical slope values (i.e., stiffness) for the early stance and late swing phase linear regression lines.

TABLE 1

Estimated Stiffness from the Linear Regression Slopes

| Gait Cycle Region | Stiffness [Nm/(kg * deg)] |
| --- | --- |
| Early Stance | 0.05563 |
| Late Swing | 0.004486 |

Using the stiffness values provided in Table 1 also allows the quantification of the stiffness variation between the stance and swing phases. For the specific case provided by Winter's data for normal cadence, it is found that the swing phase stiffness is approximately twelve times smaller than the stiffness observed for the stance phase. Nevertheless, while it may be assumed based on this data that this ratio is approximately constant for a varying body mass, it can be shown that this ratio is greatly affected by the cadence at which the estimation is performed. This last observation is sustained by the estimated stiffness provided for each cadence specified in Winter's data, as shown in Table 2.

TABLE 2

Influence of Cadence on the Knee Estimated Stiffness

| Gait Cadence [steps/min] | Gait Cycle Region | Stiffness [Nm/(kg * deg)] |
| --- | --- | --- |
| Slow (85 steps/min) | Early Stance | 0.05193 |
| | Late Swing | 0.002098 |
| Normal (105 steps/min) | Early Stance | 0.05563 |
| | Late Swing | 0.004486 |
| Fast (125 steps/min) | Early Stance | 0.06182 |
| | Late Swing | 0.006076 |

The data provided in Table 2 shows that while both stance and swing phase stiffness are increasing with cadence, swing phase knee joint stiffness is shown to increase faster than the stance phase stiffness. Since swing phase knee joint perturbations are mostly of an inertial nature, higher cadences can lead to an increased stiffness in order to maintain a satisfactory performance level and adequate synchronism. Thus, the control parameters can be compensated based on the cadence of the POD user. As mentioned previously, this compensation can be done dynamically using the dynamic trajectory compensator 125 or can be stored in the lookup table 122' of the equilibrium trajectory generator 120.

Stairs Ascent Torque-Angle Diagram

Similar to what was performed for the level walking case, it is possible to characterize knee joint gait cycle during stairs ascent using torque-angle cyclograms. While the analysis of the level walking knee joint gait cycle was sustained by the desire to characterize the relationship between knee joint dynamic stiffness and body mass, the stairs ascent analysis is more oriented towards the analysis of the stairs ascent gait cycle from an impedance standpoint and its comparison with the stiffness value found for the level walking case. In other words, it is desired to estimate the dynamic stiffness required at the knee joint in order to perform stairs ascent and relate the stairs ascent stiffness value to the stiffness value found for level walking at normal cadence.

One major difference between the level walking locomotion task and the stairs ascent locomotion task is found in the role of the knee joint itself and its contribution to the overall lower-limb dynamics. While the knee joint role during level walking is observed to be one of energy dissipation and position regulation, the knee joint role during stairs ascent is observed to present a more active contribution to the lower-limb dynamics. This difference is visible from the general appearance of the cyclogram, or more precisely the loops observed in the cyclogram. A clockwise loop in a torque-angle cyclogram corresponds to a net work absorption by the joint, while a counter-clockwise loop corresponds to a net work production by the joint. By comparing the loops found from both level walking and stairs ascent, it can be determined that the work produced by the knee joint during stairs climbing is an additional contribution.

Figure 8:
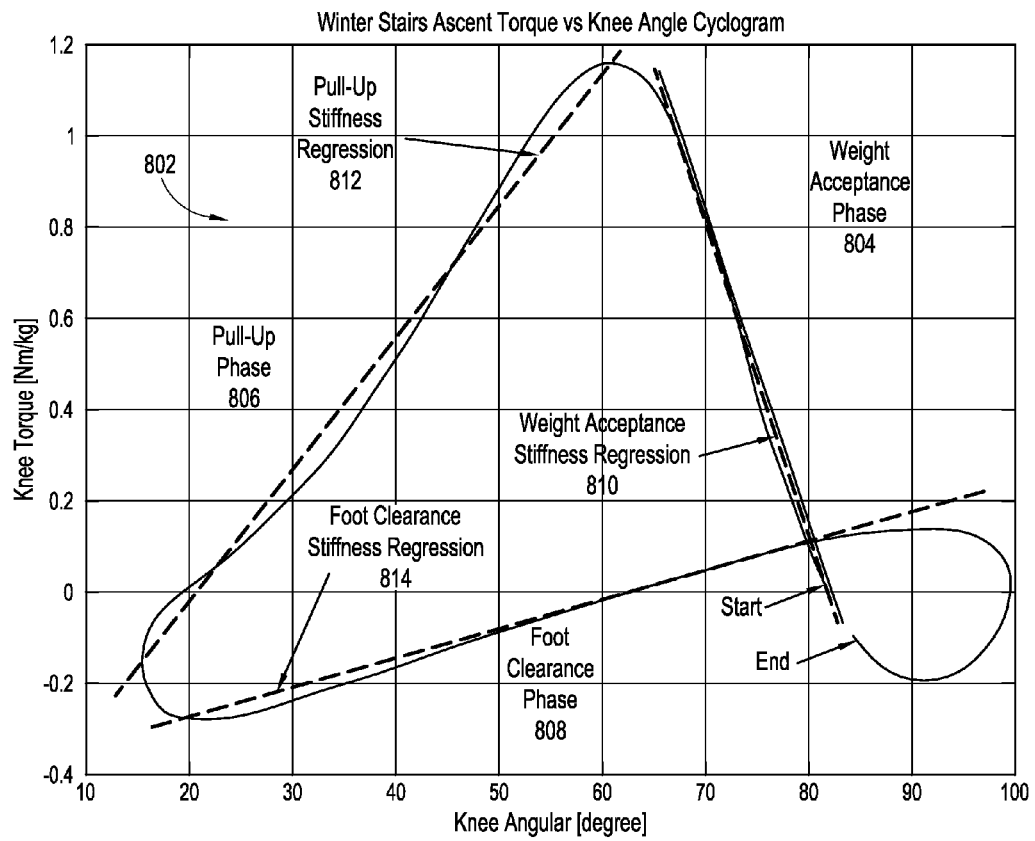
FIG. 8 is a stairs ascent cyclogram based on Winter's data.

Referring to FIG. 8, there is shown the torque-angle cyclogram 802 obtained from Winter's data for stairs ascent. The gait cycle as represented in FIG. 8 is subdivided into a weight acceptance phase 804, a pull-up phase 806 and a foot clearance phase 808. The weight acceptance 804 and pull-up 806 phases correspond to the stance phase of the gait cycle, while the foot clearance phase 808 corresponds to the swing phase.

The weight acceptance phase 804 corresponds to the completion of the foot placement and progressive weight transfer from one leg to the other. The exact shape and slope of this part of the torque-angle curve is found to vary based on the combination of voluntary movement of the joint, variation of the joint stiffness during foot placement, effect of body weight, and, finally, relative timing of these factors. The Winter-based torque-angle cyclogram 802 is characterized by the absence of any weight acceptance flexion of the joint, likely caused by a sufficient increase of the joint stiffness prior to weight transfer completion. This particular combination of events leads to a negative slope of the torque-angle linear regression line 810 in the weight acceptance phase region of the cyclogram 802. On the other hand, plotting the torque-angle characteristic using data showing weight acceptance flexion, leads to a positive slope of the linear regression line in that same part of the cyclogram. This type of gait kinematics can be found for cases where the knee joint stiffness increase is slightly delayed with respect of the weight transfer from one leg to the other or a diminished contribution of the opposite leg push off prior to toe-off.

It is then assumed that the stiffness found for the early stance phase (i.e., weight acceptance phase 804) provides a good estimate of the observed knee joint dynamic stiffness. Using the procedure defined previously, the dynamic stiffness associated to this specific gait portion, as well as the swing phase (i.e., leg pull through), are quantified by the slope of the best-fit linear regression of the torque-angle points included in the phases of the cycle. The resulting regression lines (810, 812, 814) are displayed on FIG. 8 and the linear regression parameters are provided under numerical format in Table 3.

TABLE 3

| Estimated Stiffness from the Linear Regression Slopes | |
|---|---|
| Gait Cycle Region | Stiffness [Nm/(kg * deg)] |
| Weight Acceptance | 0.07143 |
| Foot Clearance | 0.006509 |

From the data provided in Table 3, it can be observed that the knee joint dynamic stiffness estimated for the weight acceptance phase 804 in stairs ascent is found to be about 30% superior to its level walking counterpart, while the swing phase stiffness is found to be approximately 45% superior to the corresponding estimated level walking value.

Stairs Descent Torque-Angle Diagram

Figure 11:
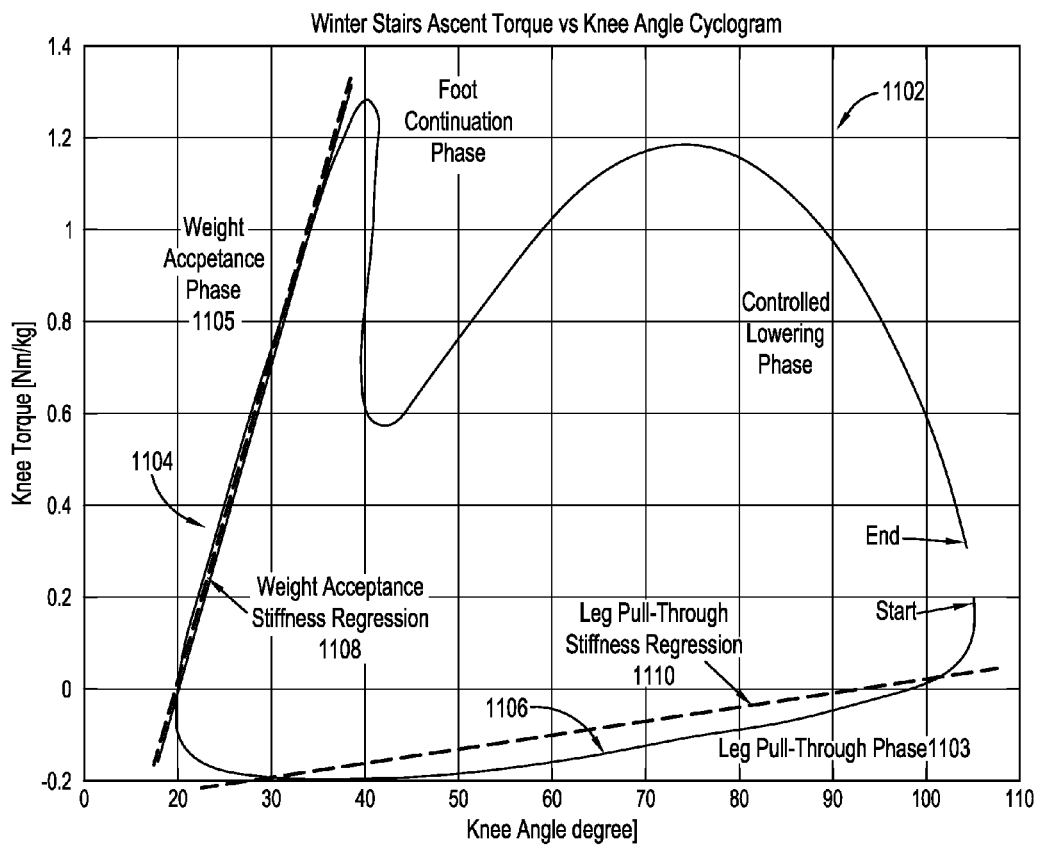
FIG. 11 is a stairs descent cyclogram based on Winter's data.

Similarly to what was performed in the case of the stairs ascent torque-angle diagram, it is possible to plot the torque-angle characteristic for the stairs descent gait task. Referring to FIG. 11, there is shown the torque-angle cyclogram obtained from Winter's data for stairs descent, along with the regressed linear trends displayed by the torque-angle data for the stance and swing phase of the gait cycle.

The stairs descent cyclogram 1102 is characterized by a single clockwise loop, corresponding to net work absorption by the joint throughout the cycle. Also, the cyclogram 1102 displays two linear trends 1104, 1106 corresponding to the swing (i.e., leg pull-through) phase 1103 and the early stance (i.e., weight acceptance) phase 1105. Again, swing phase stiffness is observed to be quite lower than the stance phase stiffness. Performing least-squares linear regression of the torque-angle points, respectively, results in the early stance linear regression line 1108 and swing phase linear regression line 1110, which leads to the slope (i.e., stiffness) values provided in Table 4.

TABLE 4

| Estimated Stiffness from the Linear Regression Slopes | |
|---|---|
| Gait Cycle Region | Stiffness [Nm/(kg * deg)] |
| Weight Acceptance | 0.07143 |
| Leg Pull Through | 0.002684 |

Comparing the weight acceptance stiffness value provided by Table 4 to the weight acceptance stiffness value found earlier for the normal cadence level walking case, it can be observed that the estimated stairs descent stiffness is higher, similar to what was found for the stairs ascent case. This can be explained by the increased loading imposed at the knee joint during stairs descent, which requires a higher stiffness level at the articulation to ensure joint stability and minimize deflection under loading. On the other hand, swing phase stiffness during stairs descent is smaller than the baseline reference value provided by the normal cadence level walking. Reduced stiffness observed during swing phase can be attributed to the quasi-passive nature of the lower-limb swing phase motion during stairs descent.

As discussed previously, based on the locomotion type determined by the locomotion recognition module, the control parameters can be adjusted. Accordingly, the knee dynamic stiffness can be adjusted when the locomotion recognition module 110 detects stair ascent and/or stair descent.

Position $\Theta_d$ Compensation
Level Walking Equilibrium Trajectories

An equilibrium trajectory for level walking can be defined that will allow the knee joint dynamic response of the motorized POD 200 (see FIG. 2A) to match the kinematics of the normal human lower-limb. The knee elastic behavior coupled to the equilibrium trajectory or static calibration model can result in normal kinematic behavior of the knee-joint. In other words, the POD 200 can be calibrated so that the observed knee joint deflection of the POD 200 approximates the Winter Reference Trajectory. Furthermore, defining equilibrium trajectories based on the knee dynamic stiffness, knee joint expected loading, and desired kinematics behavior, such as Winter Reference Trajectory, aids in simulating impedance.

Figure 4A:
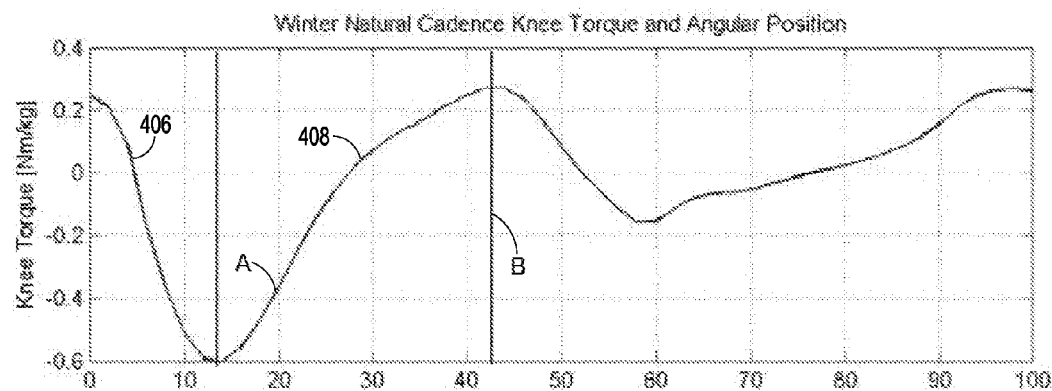
FIGS. 4A and 4B are plots of the knee torque and angular position profiles provided by Winter's data for level walking.
Figure 4B:
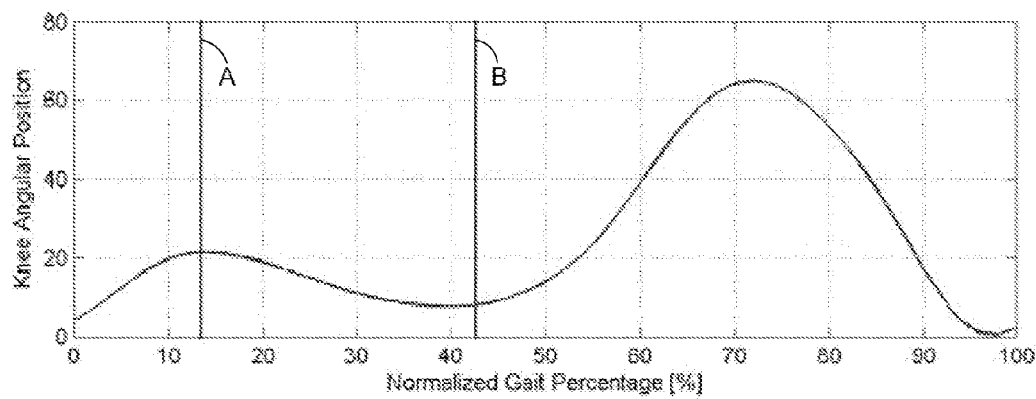

Referring to FIGS. 4A and 4B, there is shown the knee torque profile 402 (FIG. 4A) and angular position profile 404 (FIG. 4B) provided by Winter's data for level walking. It is generally accepted that the stance phase of the gait cycle represents approximately the first 50% to 60% of the gait cycle. The general equilibrium trajectory profile can be determined by looking at the knee torque profile during the stance phase of the gait cycle. First, it can be observed that the torque profile changes sign twice during the stance phase, going from positive to negative at the first point 406 and back to positive at the second point 408. Following these torque direction variations, the equilibrium trajectory can be set such that the torque variation results in corresponding deflections from the equilibrium trajectory. The first deflection can be a relative maximum deflection point (point A of FIGS. 4B, 5, and 6) and the second deflection can be a relative minimum deflection point (point A of FIGS. 4B, 5, and 6). It can further be determined that the approximate maximum/minimum torque points of the stance phase torque profile, identified as point A and point B, correspond to the first and second angular position bumps in the Winter Reference Trajectory profile (point A and point B of FIG. 6).

Referring again to FIG. 5, there is shown the level walking cyclogram 502 based on Winter's data, which provides the approximate torque-angle characteristic for the stance and swing phases of the gait cycle. The relation between torque and angular deflection during stance phase of the level walking gait cycle can generally be described as linear and is provided by an expression of the form:

$$\tau = K_\theta \cdot \Delta\theta, \quad \text{Equation 1}$$

where $\tau$ is the torque affecting the spring-like element;

$\Delta\theta$ is the angular coordinates of deflection caused by the torque; and $K_\theta$ is the relation between $\Delta\theta$ and $\tau$, and is termed rotational stiffness.

With continued reference to FIGS. 4A and 4B, points A and B in FIGS. 4A and 4B correspond to points A and B in the stance phase of the Winter Natural Cadence Torque-Angle Cyclogram for level walking, as shown in FIG. 5. Furthermore, points A and B can be described as roughly being on the same torque-angle characteristic (i.e. stiffness) linear regression. In addition, the dynamic stiffness can be considered as being approximately uniform throughout the stance phase, and can be found as the slope of the linear regression line of the stance phase torque-angle characteristic.

Using the assumptions and results provided above, the location of the equilibrium trajectory for points A and B can be computed. From FIGS. 4A and 4B, the following information for points A and B can be calculated:

$$\tau_A = -0.60 \frac{\text{Nm}}{\text{kg}}, \theta_A = 21.700°, \quad \text{Equation 2}$$

$$\tau_B = 0.27 \frac{\text{Nm}}{\text{kg}}, \theta_B = 7.725°. \quad \text{Equation 3}$$

Using the dynamic stiffness value found from the linear regression of the early stance phase of torque-angle cyclogram for level walking (Regression 512 of FIG. 5), quantified as:

$$K_\theta = 0.05563 \frac{\text{Nm}}{\text{kg} \cdot \text{deg}}, \quad \text{Equation 4}$$

the equilibrium trajectory position, $\theta_E$, for points A and B can be computed using the relation provided by Equation 1. At point A, the equilibrium trajectory position is found from:

$$\tau_A = K_\theta \cdot \Delta\theta_A = K_\theta \cdot (\theta_E - \theta_A), \quad \text{Equation 5}$$

$$\theta_E = \frac{\tau_A}{K_\theta} + \theta_A, \quad \text{Equation 6}$$

which leads to a final value of:

$$\theta_E = 10.91°. \quad \text{Equation 7}$$

Repeating the same procedure at point B:

$$\tau_B = K_\theta \cdot \Delta\theta_B = K_\theta \cdot (\theta_E - \theta_B), \quad \text{Equation 8}$$

$$\theta_E = \frac{\tau_B}{K_\theta} + \theta_B, \quad \text{Equation 9}$$

which leads to a final value of:

$$\theta_E = 12.57°. \quad \text{Equation 10}$$

From these computed values, it can be determined that the equilibrium trajectory during the stance phase can be approximated by a single amplitude. In one embodiment, the equilibrium trajectory is constant, or approximately constant, during at least a portion of the stance phase of a gait cycle. In another embodiment, the equilibrium trajectory is constant, or approximately constant, during the entire stance phase of the gait cycle. For example, equilibrium trajectory amplitudes can be 12°, or approximately 12°, during at least a portion of the stance phase of a gait cycle, or during the entire stance phase of the gait cycle. Other amplitudes can be used as well as a variable amplitude during the stance phase without departing from the spirit and scope of the description.

Figure 6:
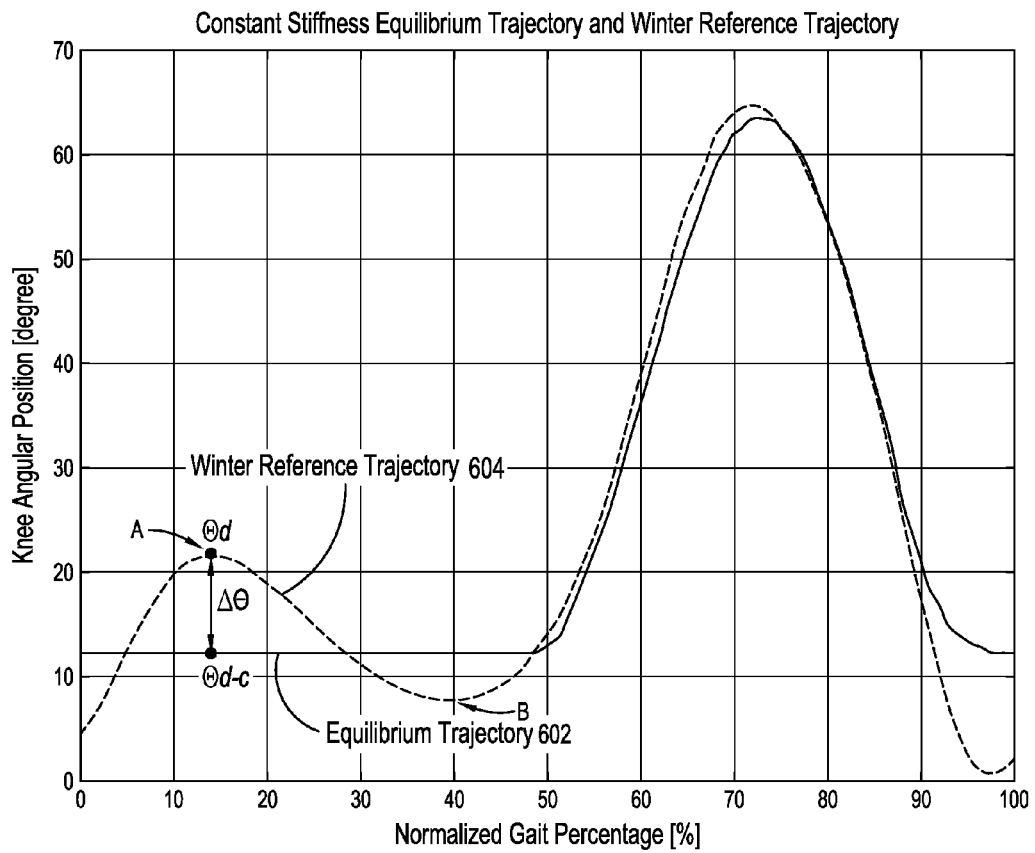
FIG. 6 is a plot of the equilibrium trajectory profile compared to the reference trajectory provided by Winter kinematics data for level walking.

Referring now to FIG. 6, there is shown a plot of the equilibrium trajectory profile 602 compared to the Winter Reference Trajectory profile 604 provided by Winter kinematics data. As illustrated, the equilibrium trajectory profile 602 differs from and does not approximate normal knee joint kinematic behavior and/or the Winter reference trajectory profile 604 during at least a portion of the stance phase of the gait cycle. In one embodiment, the equilibrium trajectory profile 602 does not approximate normal knee joint behavior during the entire stance phase.

The Winter reference trajectory profile 604 gives the desired knee joint deflection position, $\Theta_d$, during a gait cycle. The equilibrium trajectory profile 602 gives the compensated desired knee joint deflection position, $\Theta_{d-C}$, during a gait cycle. The difference, $\Delta\theta$, between the desired position, $\Theta_d$, and the compensated desired position, $\Theta_{d-C}$ can be computed using Winter reference trajectory profile 604 and the equilibrium trajectory profile 602. The equilibrium trajectory profile 602 and the compensated desired position $\Theta_{d-C}$ can further be described as input used to set the appropriate stiffness of the knee-joint so that the observed angular deflection caused by the expected torque approximates Winter reference trajectory profile 604 and the desired position $\Theta_d$. In one embodiment, it is assumed that $\Theta_{d-C} = \theta_E = 12°$ for the complete stance phase of the level walking gait cycle. However, other values for $\Theta_{d-C}$ can be used. Furthermore, $\Theta_{d-C}$ can be configured to vary during the stance phase.

Stairs Ascent Equilibrium Trajectories

Stairs ascent is another locomotion task frequently encountered in everyday life. To increase the synergy between the user and the motorized POD 200, an equilibrium trajectory for this locomotion task can be defined based on the expected knee joint loading and knee joint impedance or stiffness.

Figure 7A:
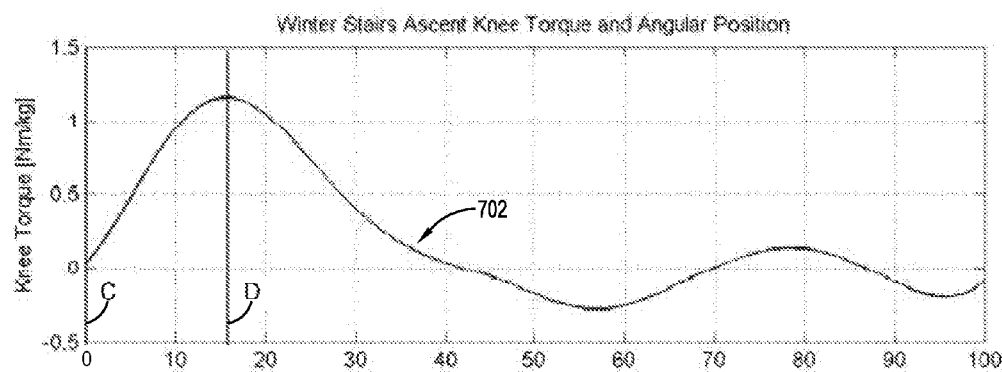
FIGS. 7A and 7B are plots of the knee torque and angular position profiles provided by Winter's data for stairs ascent.
Figure 7B:
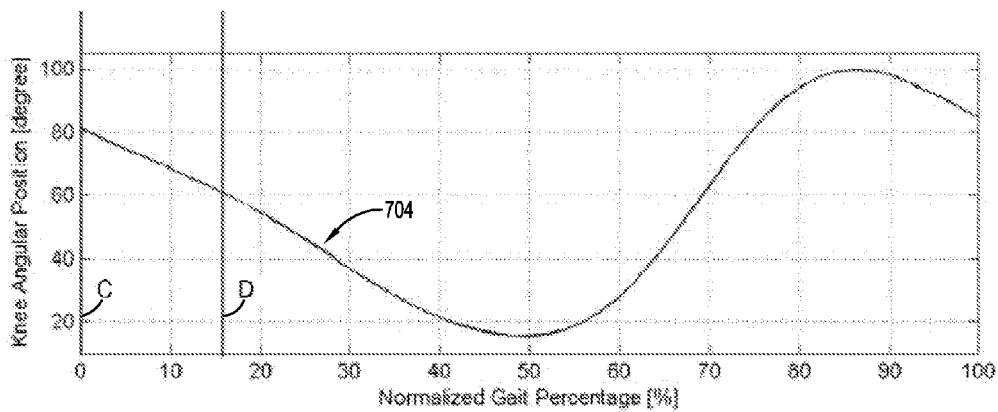

The equilibrium trajectories can be determined by observing the stairs ascent kinematics. Referring to FIGS. 7A and 7B, showing the knee torque profile 702 (FIG. 7A) and angular position profile 704 (FIG. 7B) provided by Winter's data for the stairs ascent, some gait cycle parameters can be defined to facilitate further analysis. The weight acceptance phase is included between the points C and D, and the stance phase of the stairs ascent gait cycle is generally known to last about 60% to 65% of the gait cycle, beginning with the weight acceptance phase. In one embodiment, it can be assumed that the stance phase duration represents about 40% of the gait cycle and that the knee joint dynamic stiffness is provided from the slope of the torque-angle characteristic, computed for the weight acceptance period that is considered to last from heel strike to maximum torque level. For the torque and knee angular position profiles presented in FIGS. 7A and 7B, this represents approximately the 0 to 16% section of the gait cycle.

Plotting the curves 702, 704 provided in FIGS. 7A and 7B against one another generates the torque-angle cyclogram 802 of FIG. 8. As mentioned earlier, the slope of the weight acceptance linear regression line 810 provides the value of the dynamic stiffness that is assumed to hold for the complete stance phase. In order for the knee motion to occur during stance phase of stair ascent, it is assumed that the stiffness value is maintained and the equilibrium point is moved, while elastic behavior of the knee joint is still allowed along the slope of the dynamic stiffness. In the specific context of having an amputee climb stairs using the motorized POD 200, adopting high impedance behavior for the weight acceptance can facilitate the improved completion of the task by providing increased stability and robustness. Moreover, the user can also get a better feeling of the foot-ground interaction by defining the knee joint impedance to the weight acceptance phase value. If the selected impedance is too high, then the POD 200 can affect the overall synergy between the user and the knee by initiating motion before weight transfer is completed. If the selected impedance is too low, the POD 200 can cause the user to feel as though the knee will buckle.

For level walking, the equilibrium trajectory can be defined with constant amplitude during the stance phase of the gait cycle based on the computation of the deflection levels at the maximum torque points. For stair ascent, a slightly different approach is adopted. In one embodiment, instead of computing a few points and making assumptions on the general shape of the trajectory, computations are performed for all the kinematics data points corresponding to the stance phase of the gait cycle.

Following the mathematics introduced above for the level walking case, the equilibrium trajectory can be found for all kinematics data points for stair ascent using the following relationship:

$$\theta_E = \frac{\tau_W}{K_\theta} + \theta_W, \qquad \text{Equation 11}$$

where $\tau_W$ and $\theta_W$ are respectively representing the knee torque and knee angular position provided by Winter's data; and $\theta_E$ is the actual equilibrium trajectory angular position.

$K_\theta$ is the knee joint dynamics stiffness computed from the slope of the torque-angle characteristic during weight acceptance. For stairs ascent, this value is found to be approximately $$0.07143 \frac{\text{Nm}}{\text{kg} \cdot \text{deg}}$$

from Table 3.

Figure 9:
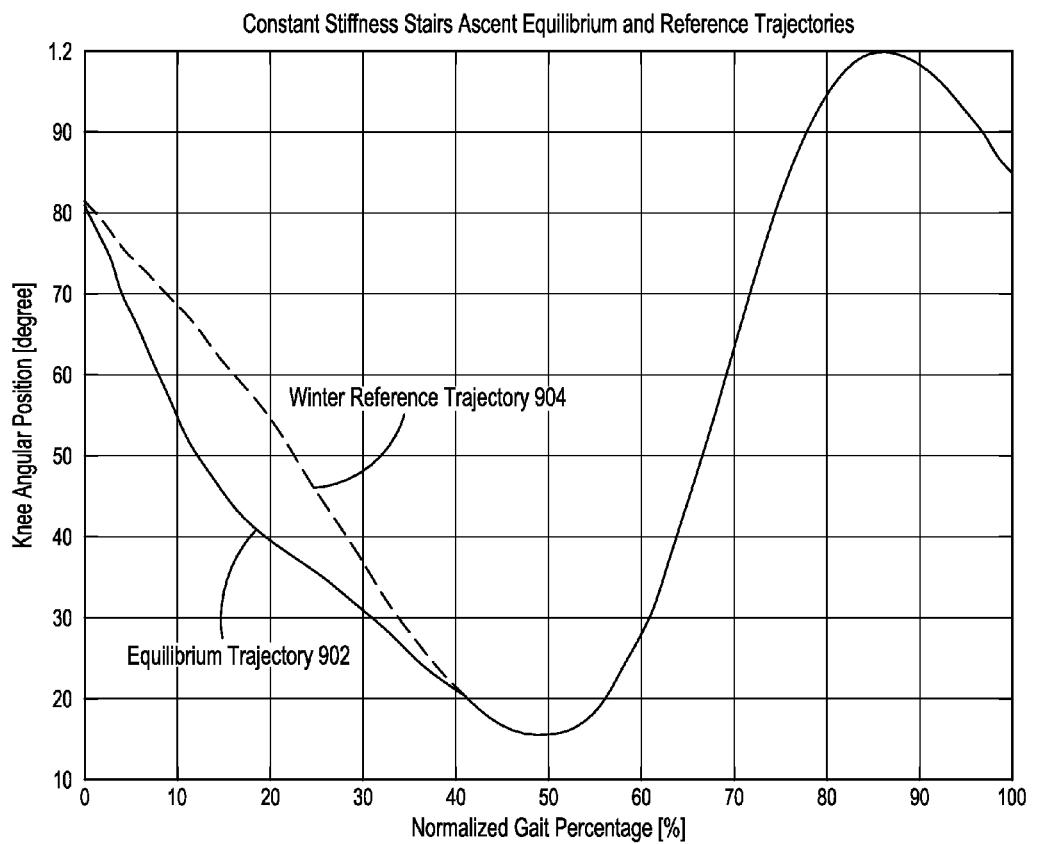
FIG. 9 is a plot of the equilibrium trajectory profile compared to the reference trajectory provided by Winter kinematics data for stairs ascent.

Using the relationship provided by Equation 11, the equilibrium trajectory location for the kinematics data points corresponding to the first 40% of the gait cycle, as represented by FIGS. 7A and 7B, can be computed. FIG. 9 illustrates the equilibrium trajectory 902, as computed, plotted against Winter's kinematics reference 904, from which it is possible to observe that the equilibrium trajectory generated displays an extension position offset with respect to the Winter reference trajectory 904. Furthermore, during at least a portion of the stance phase of the gait cycle the equilibrium trajectory 902 differs from and does not approximate normal knee joint kinematic behavior and/or the Winter reference trajectory 904.

The objective of the locomotion task is to lift the weight of the user to climb a staircase and overcome the knee joint limited stiffness. To accomplish this objective the knee joint can be "pulled" higher (i.e. in extension) than the desired kinematics reference so that the final knee joint position more closely approximates the desired kinematics reference.

Stairs Descent Equilibrium Trajectories

Stairs descent, like stairs ascent, is another locomotion task frequently encountered in everyday life. While being complementary to the stairs ascent task, some interesting similarities between the two tasks are also observed. A voluntary movement superposed to an elastic behavior also characterizes the stairs descent stance phase.

Again, an equilibrium trajectory can be established such that the use of a constant stiffness throughout the stance phase of the stairs descent generates a knee joint position response that generally follows the kinematics reference signal selected. Similar to the stairs ascent locomotion task, stairs descent stance phase is characterized by a weight acceptance elastic behavior, this time followed by a controlled lowering phase where both an elastic behavior and voluntary motion can be observed at once.

Figure 10A:
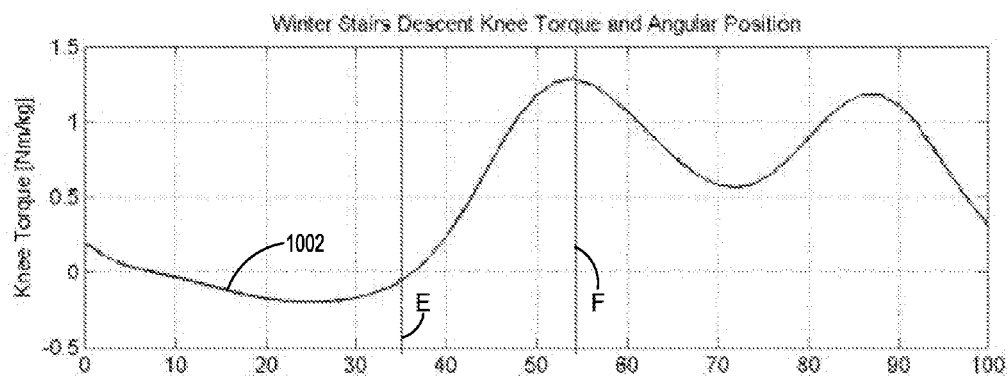
FIGS. 10A and 10B are plots of the knee torque and angular position profiles provided by Winter's data for stairs descent.
Figure 10B:
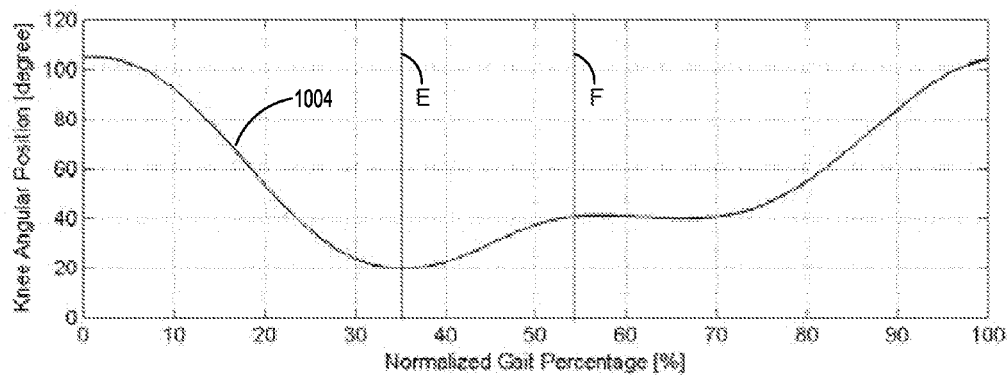

FIGS. 10A and 10B illustrate the knee torque profile 1002 (FIG. 10A) and angular position profile 1004 (FIG. 10B) provided by Winter's data for stairs descent. Using the profiles 1002, 1004, illustrated in FIGS. 10A and 10B, it is possible to define some gait cycle parameters. In contrast to FIGS. 4A, 4B, 7A, and 7B, FIGS. 10A, 10B, 11, and 12 illustrate a gait cycle with the swing phase first, followed by the stance phase.

The weight acceptance phase is included between the points E and F in the stance phase of the stairs descent gait cycle is generally known to last about 60% to 65% of the gait cycle, beginning with the weight acceptance phase.

Knee dynamic stiffness can be computed from the weight acceptance torque-angle characteristic and applied to the stance phase of the gait cycle. Referring to FIG. 11, there is shown the torque-angle cyclogram 1102 based on Winter's stairs descent data. The cyclogram 1102 is used to compute the weight acceptance phase dynamic stiffness. Computing the slope of the linear regression line 1108 of the torque-angle characteristic shown in FIG. 11 leads to a knee joint angular stiffness of approximately $$0.07143 \frac{Nm}{kg \cdot deg},$$

which is equal to the value for stairs ascent. As for stairs ascent, it is assumed that the weight acceptance phase is the only purely elastic phase of the gait cycle. The remaining part of the stance can be characterized by the same type of elastic behavior (i.e., dynamic stiffness). Similar to stair ascent, the equilibrium point can be moved in order to control the lowering of the body centre of mass. The weight acceptance, high impedance can be maintained over the whole stance phase since the resulting knee joint dynamic behavior is expected to be more stable and provide a better feeling of the foot-ground interaction to the prosthesis user.

Figure 12:
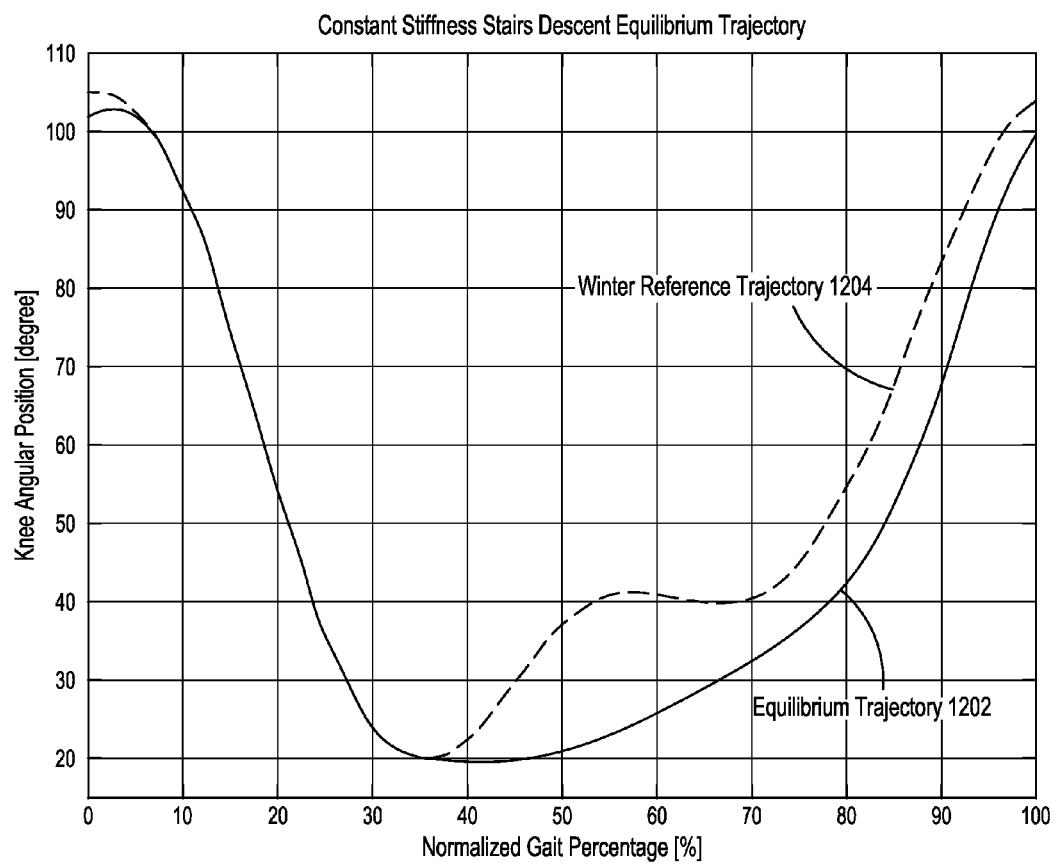
FIG. 12 is a plot of the equilibrium trajectory profile compared to the reference trajectory provided by Winter kinematics data for stairs descent.

Applying Equation 11 to the torque values, Winter's data points illustrated in FIG. 10A, and the dynamic stiffness value specified above generates the equilibrium trajectory 1202 presented in FIG. 12.

The equilibrium trajectory 1202 shows an offset with respect to Winter's trajectory 1204 for the complete stance phase, due to the amplitude of the perturbation torque, such as user body mass for example, over that complete gait phase. Furthermore, during at least a portion of the stance phase of the gait cycle the equilibrium trajectory 1202 differs from and does not approximate normal knee joint kinematic behavior and/or the Winter reference trajectory 1204. As it was observed for the stairs ascent equilibrium trajectory, the equilibrium trajectory 1202 displays an angular position extension offset in order to "pull" the thigh upwards and support the whole body weight against the effects of gravity. This offset can compensate for the deflection caused by the torque imposed at the articulation and the non-infinite stiffness of the joint.

Calibration Model

To facilitate the motorized POD 200 configuration and reduce set-up time, the basic controller gain values, i.e. $K_P$ and $K_D$, can be correlated to user physiological characteristics. In this way, the prosthetist is provided with a framework from which to start the adjustment and tuning of the motorized POD device 200.

Proportional Gain

The controller compensated proportional gain, i.e. $K_{P-C}$, is the controller term that affects the control signal based on the position error, which is the difference between the equilibrium position and the actual system position. This specific parameter is termed proportional gain since it actually increases the control signal proportionally to the measured error signal. Hence, as the position error increases, the control signal is proportionally increased. This generates an overall behavior similar to spring stiffness, since the control signal is generally expressed as a generalized force and is found proportional to the position error amplitude.

The basic proportional gain value $K_{P-C}$ can be set-up at system initial configuration based on the user body mass (including the motorized POD 200), as provided to the system by the trained professional performing the system set-up. The proportional gain $K_{P-C}$ value can be adjusted to the value corresponding to the normal cadence level walking physiological knee joint dynamic stiffness, as provided in Table 1. Nevertheless, since the knee joint is actually powered using a linear actuator and controlled using an actuator space position controller, the joint space stiffness found in Table 1 can be expressed in actuator coordinates, such that the resulting stiffness value can be directly used in the low-level control law.

To convert the joint space stiffness values found in Table 1 to actuator space the following definition can be used:

$$K_A \left[ \frac{N}{m \cdot kg} \right] = K_\theta \left[ \frac{N}{deg \cdot kg} \right] * f(\theta, \tau, \ldots ). \quad \text{Equation 12}$$

where, $K_A$ and $K_\theta$, are the equivalent actuator and joint stiffness, respectively.

To relate the joint and actuator spaces stiffness, as expressed by Equation 12, both the kinematics and kinetics relationships can be merged. Use of a linearizing term based on the reflected inertia at the actuator and allowing the modification of the controller gains based on the actual actuator position can provide a desired linearization. In that context, the static calibration definition is oriented towards providing a reasonable estimate of the knee joint stiffness. The conversion factor between both coordinate system stiffness at the system neutral point can be computed and it can be inferred that the linearization scheme compensates over the remaining motion range.

Figure 13:
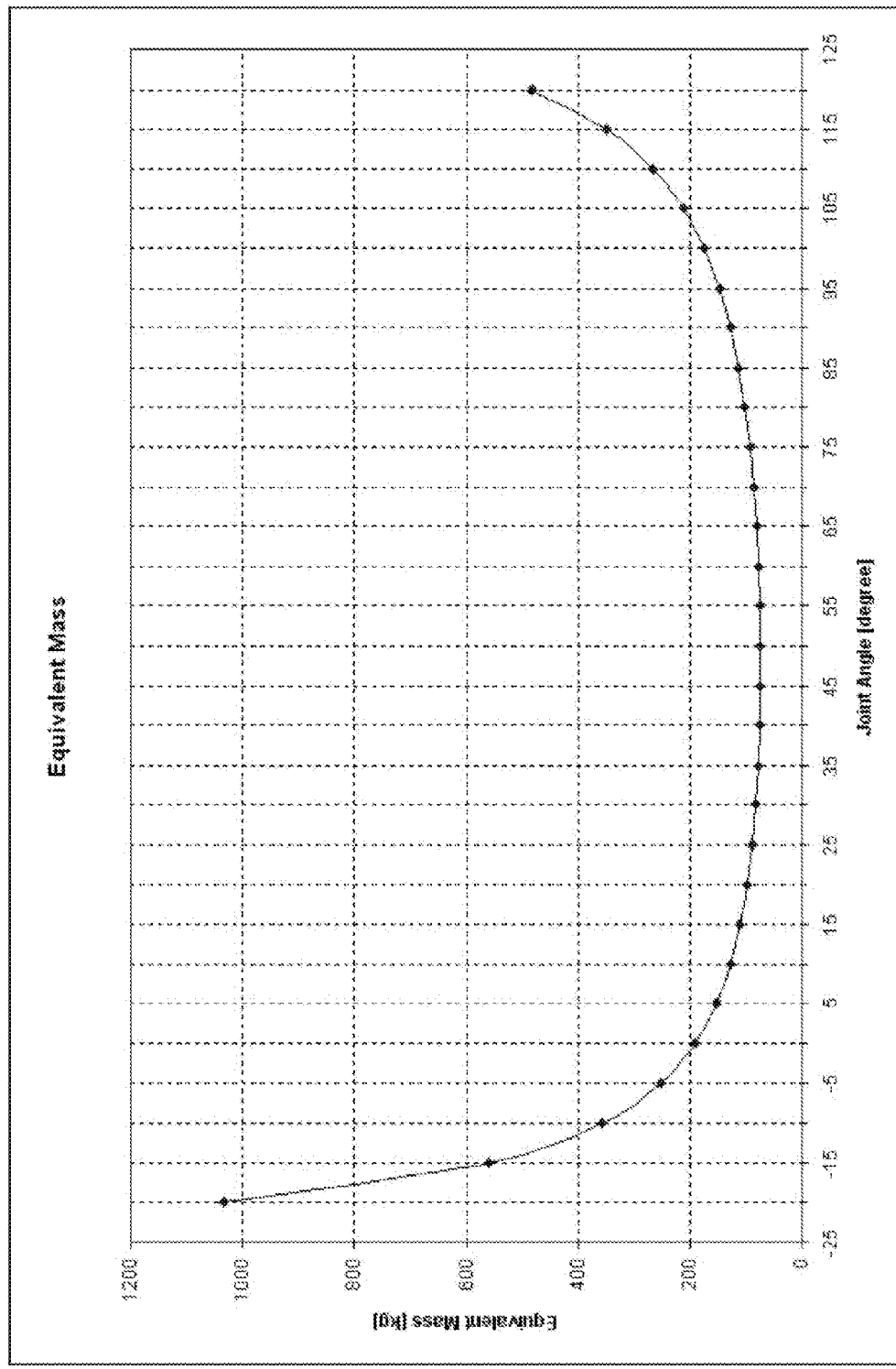
FIG. 13 is a plot of the equivalent mass linearization scheme as a function of joint angle degree.

For the motorized POD 200 system definition, the conversion factor can be computed for the position corresponding to the lowest equivalent mass at the actuator (i.e., unitary normalized equivalent mass) as illustrated in FIG. 13. For the assumptions provided above, and by expressing $K_A$ as the compensated controller proportional gain $K_{P-C}$, Equation 12 reduces to:

$$K_{P-C} \left[ \frac{N}{m \cdot kg} \right] = K_\theta \left[ \frac{N}{deg \cdot kg} \right] * \Omega \left[ \frac{N \cdot deg}{m \cdot Nm} \right]. \quad \text{Equation 13}$$

where $\Omega$ is the average conversion factor found for the position specified above.

The analysis of the equivalent mass linearization scheme as a function of joint angle degree is illustrated in FIG. 13. Further analysis leads to an unitary normalized equivalent mass point located at 49.9565°, following the usual convention (i.e., knee flexion is a positive angle with origin at full extension). For this last point of the motion range, the following equivalence are found from the kinematics and static analysis:

$$1 Nm = -20.0619 N, \text{ and} \quad \text{Equation 14}$$

$$1° = 0.0009 m. \quad \text{Equation 15}$$

Using the above average equivalence, the average conversion factor can be calculated:

$$\Omega = 22291 \left[ \frac{N \cdot \deg}{m \cdot Nm} \right].\qquad\text{Equation 16}$$

Equation 16 can be used to express the values found in Table 1 in actuator coordinates, as well as in controller gains. Multiplying the early stance stiffness value found in Table 1 with the conversion factor provided by Equation 16 leads to the following static calibration relationship:

$$K_{P\text{-}C}\left[\frac{N}{m}\right] = 1240.05\left[\frac{N}{m \cdot kg}\right] * M_B [kg].\qquad\text{Equation 17}$$

where
$K_{P\text{-}C}$ is the compensated controller proportional gain value;
$M_B$ is the body mass of the prosthesis user; and $$1240.05\left[\frac{N}{m \cdot kg}\right]$$

is the normal cadence level walking early stance phase dynamic stiffness value, found in Table 1 and expressed in the actuator coordinates system.

Derivative Gain

The controller derivative gain, i.e. $K_D$, is the controller term that affects the controller output based on the velocity of the error signal, which is the variation of the error signal between two consecutive discrete samples. Assuming that the closed-loop system behaves like a second-order system, this controller gain is also termed damping, since, in a second-order system, damping is seen proportional to the input signal velocity.

The calibration value of the controller derivative gain can be determined based on the desired system behavior. In selecting the calibration procedure, the ability to modulate the knee joint stiffness in order to accommodate a wider range of user body mass (including the motorized POD 200) can be taken into account. However, the knee joint dynamic behavior does not vary with mass and the controller is responsible to enforce the dynamic behavior.

From control theory, it is known that a second-order system dynamic behavior is defined by the controller gains coupled to the system inherent dynamic properties. The system dynamic properties resulting of the combination of both elements are known to be related through theoretical relations. Using these relations, the controller derivative gain can be computed based both on the proportional gain value found from the torque-angle cyclogram and the desired system behavior.

Second-order systems are uniquely defined by their stiffness k, mass m, and damping ratio $\zeta$, which are related through the following relations. The natural undamped frequency of a mass-spring second-order system is given by:

$$\omega_N = \sqrt{\frac{k}{m}}.\qquad\text{Equation 18}$$

The system critical damping value associated with the behavior found at the border between oscillatory and non-oscillatory behavior is found from:

$$C_C = 2m\sqrt{\frac{k}{m}},\qquad\text{Equation 19}$$

while the damping ratio is found as the ratio of the actual system damping to the critical damping:

$$\zeta = \frac{C}{C_C}.\qquad\text{Equation 20}$$

Assuming that the knee joint, or actuator, space damping is caused both by the derivative gain of the controller and the natural damping found in the mechanical linkages, the actual actuator space damping can be approximated using the following relation:

$$C = \frac{K_{D\text{-}C}}{\frac{1}{\Delta t}}.\qquad\text{Equation 21}$$

where
$K_{D\text{-}C}$ is the actual compensated controller derivative gain, found from the experimental tuning of the controller gain.

The control gains can be tuned to reach system behavior that sufficiently meets desired performance levels. It can then be inferred that the controller imposed damping, superposed to the constant natural system damping, provides the desired damping level for the system (i.e., system dynamic response). The desired amount of controller imposed damping (i.e., $K_{D\text{-}C}$) can then be quantified by specifying the system desired damping ratio. The amount of controller imposed damping can be used to compute the controller gain given the proportional gain. A system characterized by a damping ratio of:

$$\zeta_D = 0.734\qquad\text{Equation 22}$$

can generate a satisfactory knee joint behavior throughout the operational range of the motorized POD 200. Other values can be used without departing from the spirit and scope of the description. Defining the controller derivative gain static calibration value can then be expressed as defining a system damping value such that:

$$K_{D\text{-}C}\left[\frac{N \cdot \Delta t}{m}\right] = f(K_A, M_B, \zeta_D).\qquad\text{Equation 23}$$

Using the relations provided by Equations 19 to 22, the general relationship expressed by Equation 23 can be specified as:

$$C = \zeta \cdot C_C = \zeta_D \cdot 2m\sqrt{\frac{k}{m}},\qquad\text{Equation 24}$$

where
m is the actual system mass (i.e., inertia) expressed in actuator coordinates;

$\zeta_D$ is the desired damping ratio; and k is the actual actuator stiffness (i.e., controller proportional gain) found from the static calibration procedure depicted above.

Substituting the stiffness value found in this last relation by the body mass normalized value defining the proportional gain calibration introduces both the $K_A$ and $M_B$ terms in Equation 24. Performing this last substitution leads to:

$$C = \zeta_D \cdot 2m \sqrt{\frac{K_A}{m}} \cdot \sqrt{M_B}, \quad \text{Equation 25}$$

which represents the continuous time equivalent damping at the actuator, expressed in actuator coordinates. Finally, this last damping value relates to the discrete-time controller derivative gain through:

$$K_{D-C}\left[\frac{N \cdot \Delta t}{m}\right] = \frac{\zeta_D}{\Delta t} \cdot 2m \sqrt{\frac{K_A}{m}} \cdot \sqrt{M_B}, \quad \text{Equation 26}$$

where $\Delta t$ is the controller sampling period duration in seconds and allows the conversion of the continuous time domain damping value to its corresponding discrete-time equivalent controller gain. The system mass, m, is found from the analysis of the system dynamics and is taken as the normalization value of the linearization relation previously established. In the illustrative embodiment of the motorized POD 200, this value is set to 75 kg and it is assumed that the linearization procedure used with the controller allow the use of this single value in order to define the controller derivative gain. However, other values can be used without departing from the spirit and scope of the description It is now possible to formulate the derivative gain calibration relation itself, based on the following parameters:

$$\frac{1}{\Delta t} = 1320 \text{ Hz}, \quad \text{Equation 27}$$

$$m = 75 \text{ kg}, \quad \text{Equation 28}$$

$$K_A = 1240.05 \frac{N}{m \cdot \text{kg}}, \quad \text{Equation 29}$$

and the desired damping ratio provided by Equation 22, which leads to the following calibration relation:

$$K_{D-C}\left[\frac{N \cdot \Delta t}{m}\right] = 591029.8 \left[\frac{N \cdot \Delta t}{m \cdot \sqrt{\text{kg}}}\right] * \sqrt{M_B[\text{kg}]}. \quad \text{Equation 30}$$

Relations provided by Equation 17 and Equation 30 are forming what is herein referred to as the static calibration of the motorized POD system, allowing to link the impedance simulating controller gains to the user body mass in order to achieve the desired system behavior.

Dynamic Gain Tuner

Figure 14:
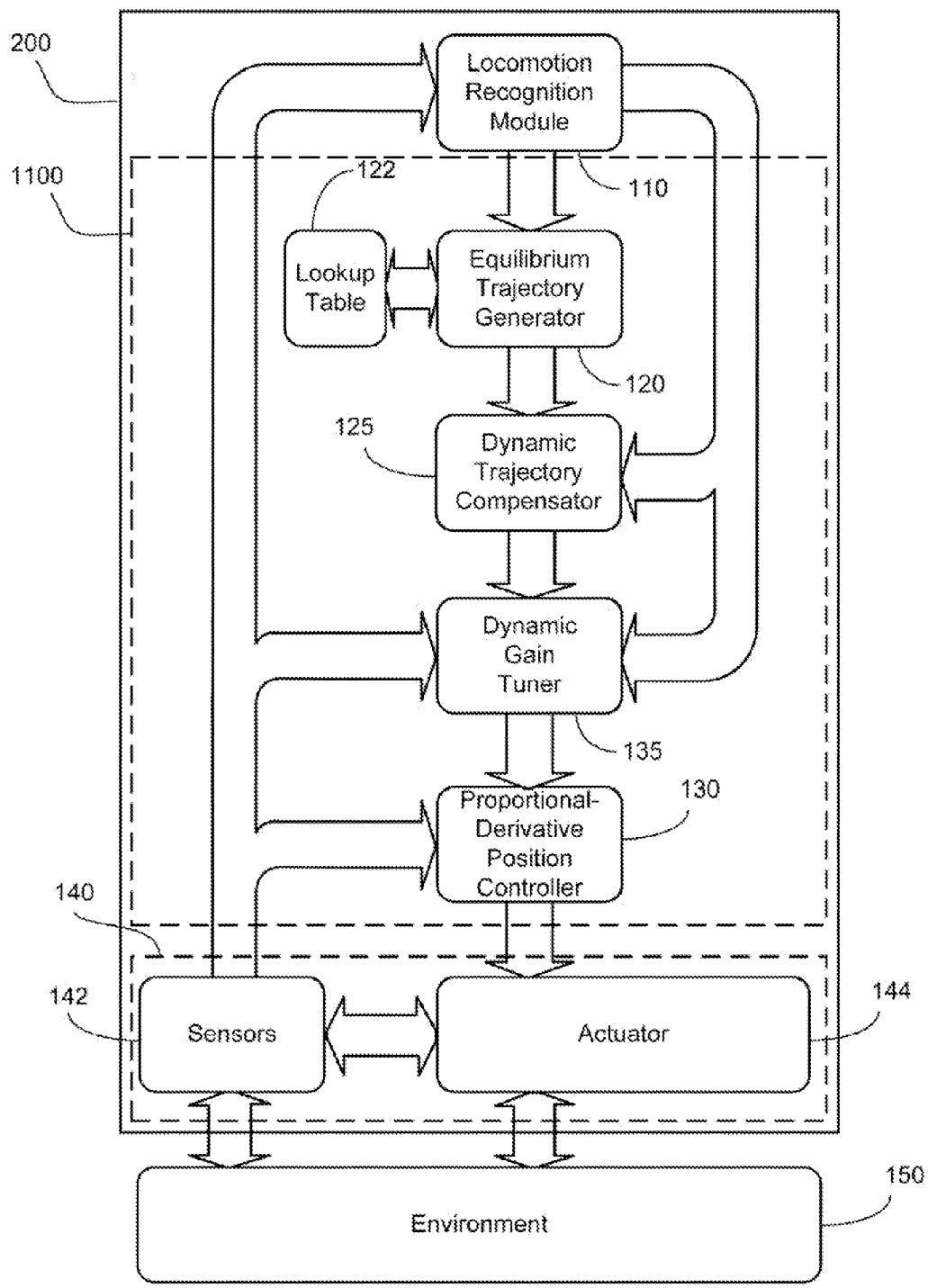
FIG. 14, is a block diagram of an alternative embodiment of the impedance simulating motion controller of FIG. 2A, which includes a dynamic gain tuner according to an embodiment.
Figure 15:
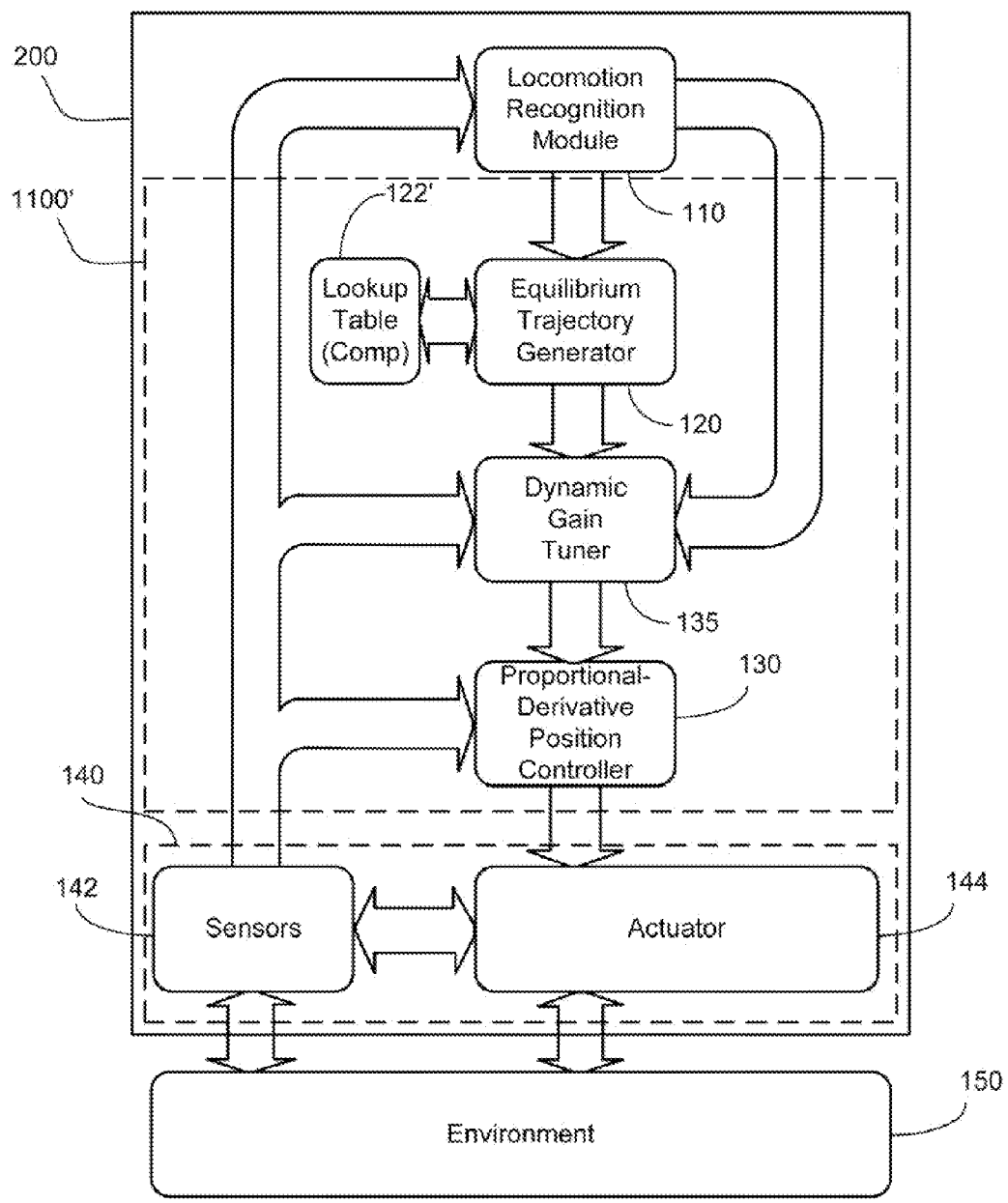
FIG. 15, is a block diagram of an alternative embodiment of the impedance simulating motion controller of FIG. 2B, which includes a dynamic gain tuner.

Referring to FIG. 14, there is shown a block diagram of an alternative embodiment of the impedance simulating motion controllers 100 of FIG. 2A. The impedance simulating motion controller 1100 of FIG. 14 is of a structure similar to that of the impedance simulating motion controller 100 of FIG. 2A with a dynamic gain tuner 135 interposed between the dynamic trajectory compensator 125 and the proportional derivative position controller 130. Similarly, FIG. 15 shows a block diagram of an alternative embodiment of the impedance simulating motion controller 100' of FIG. 2B. The impedance simulating motion controller 1100' of FIG. 15 being of a structure similar to that of the impedance simulating motion controller 100' of FIG. 2B with a dynamic gain tuner 135 interposed between the equilibrium trajectory generator 120 and the proportional derivative position controller 130.

Figure 16:
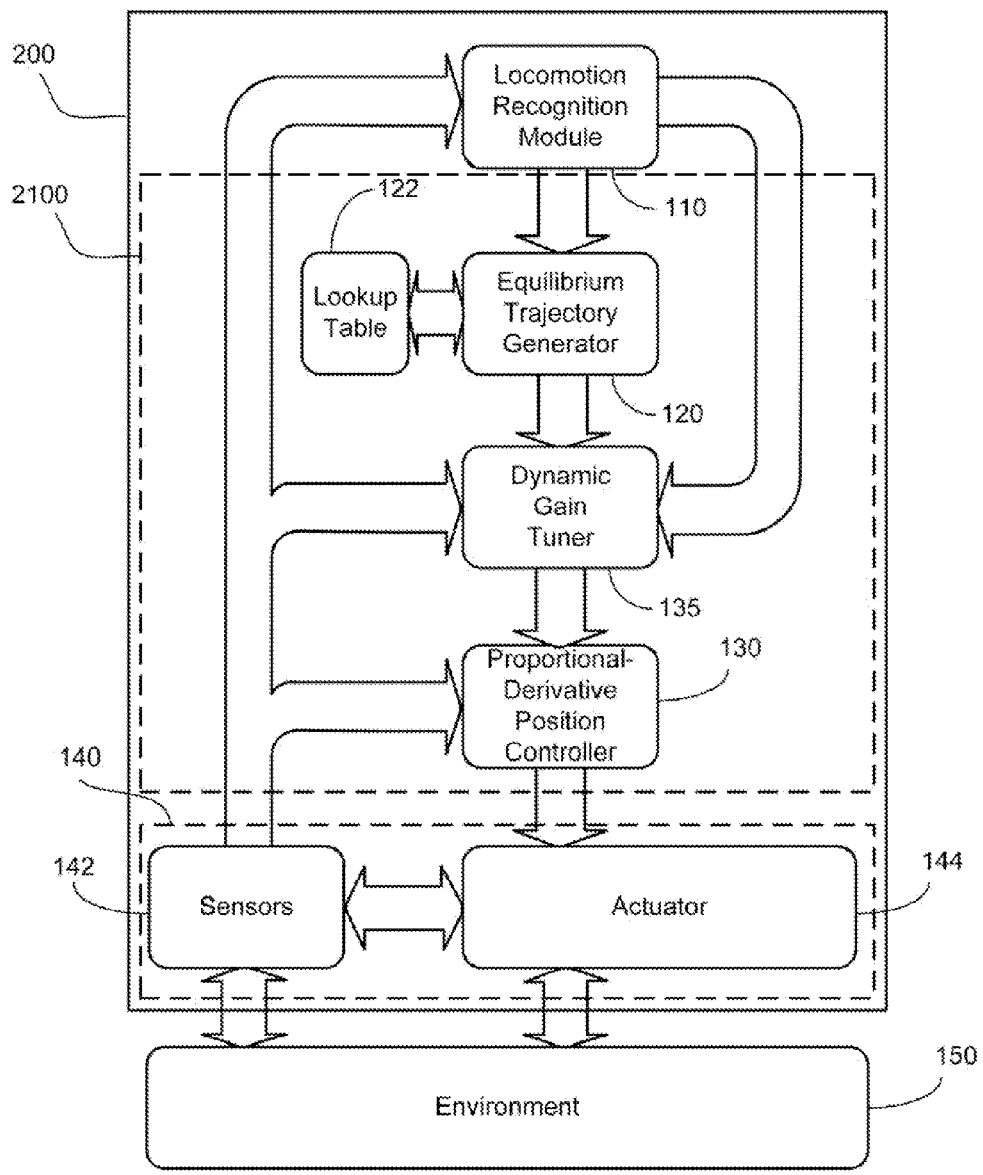
FIG. 16, is a block diagram of a motorized POD which comprises a motion controller that includes a dynamic gain tuner.

In a further alternative embodiment, illustrated in FIG. 16, the dynamic gain tuner 135 may be used independently of the dynamic trajectory compensator 125 of the impedance simulating motion controller 100 (see FIG. 2A) or the compensated lookup table 122' of the impedance simulating motion controllers 100' (see FIG. 2B), resulting in motion controller 2100.

The general objective of the dynamic gain tuner 135 is to dynamically modify the compensated control parameters received from the dynamic trajectory compensator 125, or to modify the control parameters received from the equilibrium trajectory 120, to generate tuned control parameters. Thus, in one embodiment the dynamic gain tuner 135 modifies the compensated proportional $K_{P-C}$ and derivative $K_{D-C}$ gains of the dynamic trajectory compensator 125 (in the case of the impedance simulating motion controller 1100 of FIG. 14) to generate the tuned control parameters. In another embodiment, the dynamic gain 135 modifies the proportional and derivative gains of the equilibrium trajectory generator 120 (in the case of the impedance simulating motion controller 1100' of FIG. 15) to generate the tuned control parameters. The dynamic gain tuner can be configured to modify the proportional and derivative gains, or the compensated proportional and derivative gains, in real-time (e.g. during regular joint operation, such as walking or other movement, or during and between gait cycles) such that the motorized POD 200 position response follows the general profile provided by a kinematics reference signal, regardless of changes to the user's characteristics. With regard to the motion controller 2100 of FIG. 16, the general objective of the dynamic gain tuner 135 is to modify the proportional gain $K_P$ and derivative gain $K_D$ received from the equilibrium trajectory generator 120. The dynamic gain tuner 135 can use the data received directly from the sensors 142 and the locomotion data received from the locomotion recognition module 110 to determine how to modify the proportional gain $K_P$ and derivative gain $K_D$ received from the equilibrium trajectory generator 120. In one embodiment, the sensor data and locomotion data comes directly from the sensors 142 and the locomotion recognition module 110. In another embodiment, the sensor data and the locomotion data is received by the dynamic gain tuner 135 via the equilibrium trajectory generator 120 and/or the dynamic trajectory compensator 125. Furthermore, using the data from the locomotion recognition module 110, the dynamic gain tuner 135 can determine whether the POD is in a stance phase. If the POD is not in a stance phase, the dynamic gain tuner 135 can ignore the sensor data. If the POD is in a stance phase, the dynamic gain tuner 135 can use the sensor data to determine how to tune the control parameters.

In other words, the dynamic gain tuner 135 can be represented as a criteria-based optimization process, which adjusts the knee joint behavior of the motorized POD 200 in order to approximate, or match, a predefined reference value. The dynamic gain tuner 135 can perform this optimization process during, regular joint operation, such as between gait cycles while the user is moving. In other words, the user does not need to stop to calibrate the POD in order for the dynamic gain tuner 135 to properly tune the control parameters. The dynamic gain tuner can automatically tune the control parameters while the POD is in use (e.g. when the POD user is walking). The tuning can occur between gait cycles during regular joint operation, for example while the user is walking or otherwise moving.

Thus, in one embodiment the POD can be calibrated specifically for a user based on the user's physiological characteristics, such as body weight. In this manner, the controller can compensate for the user's physiological characteristics without having to make the calculations in real-time, i.e. while the user is actively using the POD. The dynamic trajectory compensator 125 can be used for this purpose. Alternatively, the compensated values, or compensated control parameters, can be stored in a lookup table, similar to the compensated lookup table 122', illustrated in FIGS. 2 and 15. In this embodiment, the dynamic trajectory compensator can be removed, as illustrated in FIG. 2.

Furthermore, when a user carries an object, the weight of the object can affect the knee deflection. Without additional compensation for the added weight, the gait of the user can be adversely affected. The dynamic gain tuner 135 can be used to modify the gain values in order to account for the additional weight of the object, which is not compensated for by the lookup table 122' or the dynamic trajectory compensator 125. To accomplish this task, the dynamic gain tuner 135 can monitor the difference between the expected deflection value and the measured deflection value and tune the proportional gain $K_P$ and derivative gain $K_D$ to approximate, or match, the measured deflection with a predefined reference value. Alternatively, the dynamic gain tuner 135 can be used to compensate for both the weight of the object and the user's weight and can calculate the desired gain values based on real-time measurements. In this embodiment, the POD can be used without prior user-specific calibration, and the dynamic gain tuner 135 can adjust the control parameters based on the real-time physiological characteristics of the user and/or the gain scaling factor. Thus, in one embodiment, the dynamic trajectory generator 125 can be removed.

In one embodiment, the tuning by the dynamic gain tuner 135 can be performed at an integer multiple of the impedance simulating motion controller 1100, 1100' and controller 2100 sampling frequency, hence reducing the computational burden associated with this specific task.

Correction of the compensated proportional $K_{P-C}$ and derivative $K_{D-C}$ gains (or proportional $K_P$ and derivative $K_D$ gains) can be performed at every gait cycle by applying a gain scaling factor $K_C$ based on the computation of the maximal measured deflection value from an equilibrium trajectory found during the knee joint loading region of the stance phase gait cycle. Computing the gain scaling factor $K_C$ correction once every gait cycle allows for the modeling of the expected deflection as a function of the gait cadence and, therefore, does not require the generation of the kinematics reference value for all sampling instances associated with the gait cycle.

Figure 17:
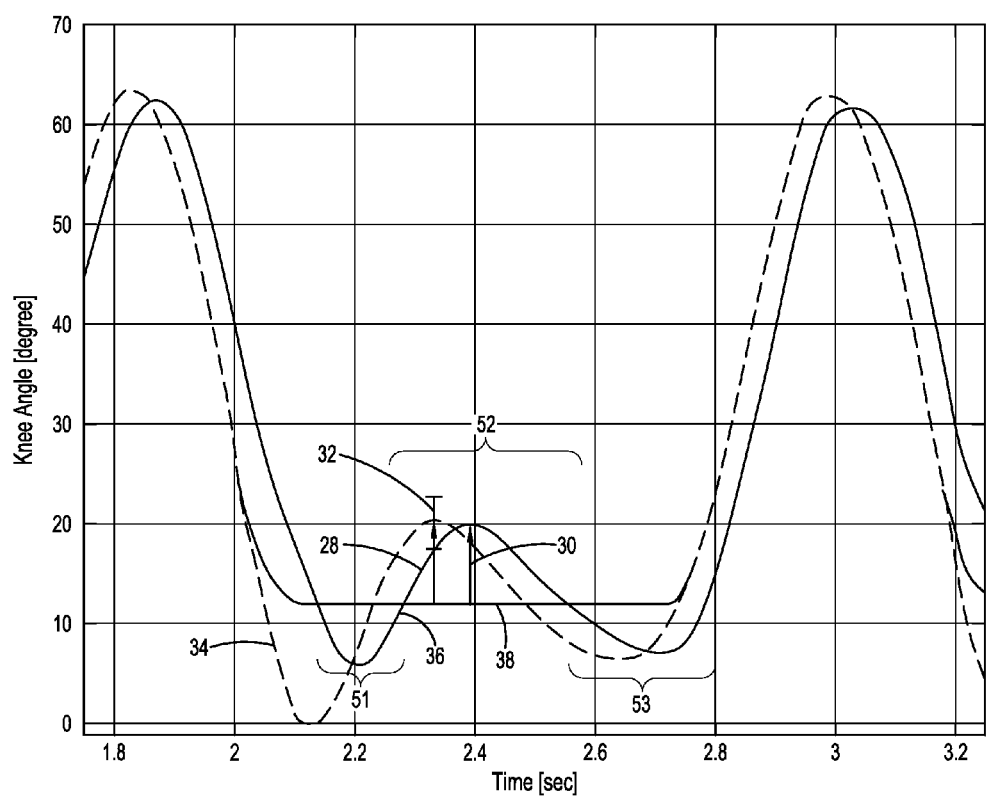
FIG. 17 is a plot defining the principal dynamics tuning parameters for the position response during level walking.

As previously mentioned, computation of the gain scaling factor $K_C$ can be calculated based on the performance of the motorized POD 200 as measured during the stance phase of the level-walking gait cycle. FIG. 17 defines the dynamic tuning parameters for the position response during level walking. Three quantities are identified: the expected deflection 28, the maximal measured deflection 30 and the tolerance.

The expected deflection 28 represents the normal, or expected, amount of deflection caused by the dynamic loading of the joint as the foot comes into contact with the ground surface and the overall dynamic and static body weight is transferred from one leg to the other. This represents the performance criteria for what is considered a normal gait stance phase and can be computed from standard kinematics reference data 34 and the specific equilibrium trajectory 38.

The maximal measured deflection 30 represents performance of the motorized POD 200 in the actual operational context. The maximal measured deflection 30 is quantified over the whole stance phase where the measured response 36 of the motorized POD 200 is superior to the equilibrium trajectory 38 (i.e., second overshoot region of the system response). This definition of the stance loading region assumes that the compensated proportional $K_{P-C}$ and derivative $K_{D-C}$ gains (or proportional $K_P$ and derivative $K_D$ gains) have been preliminary adjusted to physically relevant values, which allow the observation of a typical motorized POD 200 response 36. Although described as a maximal measured deflection, the measured deflection need not be a maximum point, but can be some other predefined point at which measurements are taken.

The tolerance is used to define a tolerance zone 32, around the expected deflection 28 where the motorized POD 200 is judged to be performing adequately. The upper and lower bounds of the tolerance zone can be referred to as tolerance levels. The combination of the expected deflection 28 with the tolerance, expressed as a percentage of tolerance, generates an envelope of valid motorized POD 200 position responses in which the tuning process of the dynamic gain tuner 135 can be inhibited. The tolerance parameter is used in order to relax the expected deflection 28 stiffness tracking by the dynamic gain tuner 135, since the expected deflection 28 for a given cadence, as well as the kinematics reference data 34 from which this criteria was computed, may not be representative of the gait style and characteristic of a specific user of the motorized POD 200. In one embodiment, when a measured deflection value falls within the tolerance zone 32, the controller does not attempt to modify, or tune, the control parameters. However, if the measured deflection falls below the lower tolerance level or above the upper tolerance level, the control parameter can be modified and/or tuned by the dynamic gain tuner 135, as described in greater detail above.

Since Winter's kinematics data is used as the kinematics reference data 34 to compute the expected deflection 28, the tolerance is used to represent the statistical spread of the normalized data. The tolerance is defined as a strictly positive quantity and the boundaries of the tolerance envelope, or zone 32, are determined by adding and subtracting the tolerance multiplied by the expected deflection 28 from the expected deflection 28 i.e. tolerance zone=expected deflection±tolerance*expected deflection. In one embodiment, the control parameters are modified and/or tuned when the measured deflection values fall below, or exceed, predefined tolerance levels, or are outside the tolerance zone 32.

Expected Deflection

Figure 18:
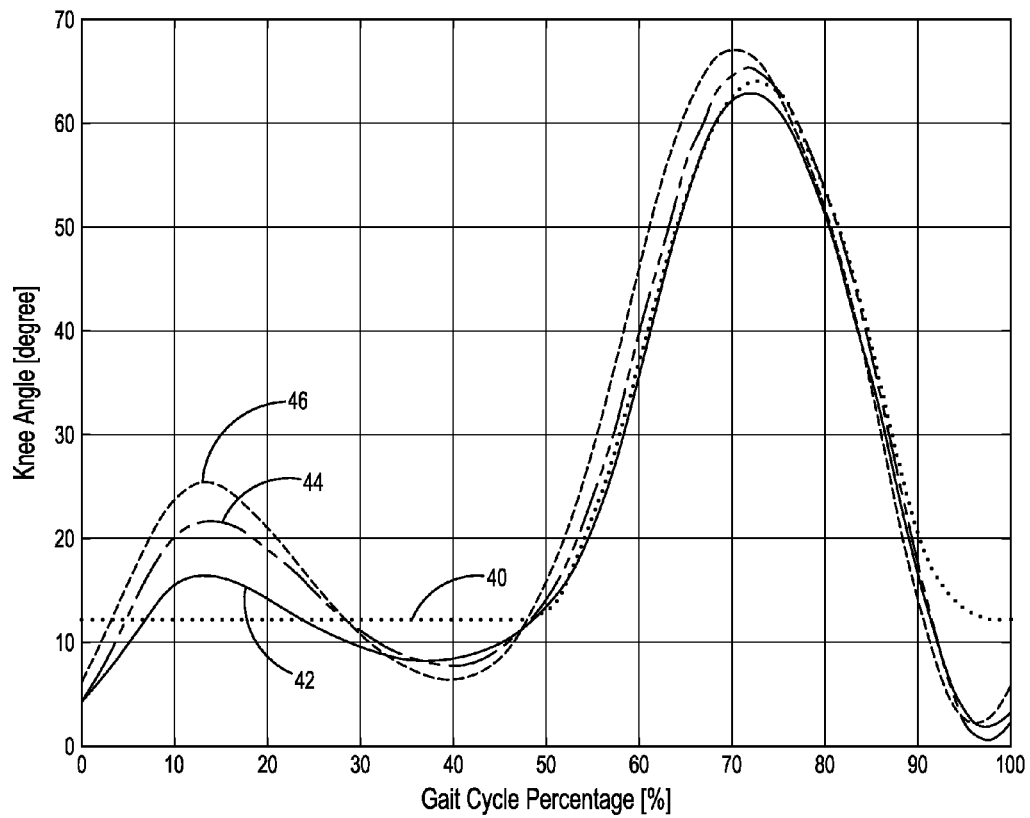
FIG. 18 is a plot of the selected equilibrium trajectory together with the kinematics reference position trajectories for slow, normal and fast gait cadences.

As previously mentioned, the expected deflection is based on a standard kinematics reference. For instance, Winter's kinematics data can be used in order to define the profile of the expected deflection. However, it is to be understood that data other than Winter's kinematics data can also be used to define the profile of the expected deflection without departing from the spirit and scope of the description. Referring to FIG. 18, there is shown the selected equilibrium trajectory 40 together with the kinematics reference position trajectories for slow 42, normal 44 and fast 46 gait cadences. By analyzing the various plots of FIG. 18, the expected deflection as a function of the gait cadence 42, 44 and 46 can be computed.

Using the plots from FIG. 18 and setting the slow gait cadence at 85 steps/min, the normal gait cadence at 105 steps/min and the fast gait cadence at 125 steps/min, Table 5 is obtained.

TABLE 5

Knee Joint Expected Deflections for Winter's Cadences

| Cadence [steps/min] | Expected Deflection [deg] |
|---|---|
| 85 | 4.2 |
| 105 | 9.67 |
| 125 | 13.24 |

Figure 19:
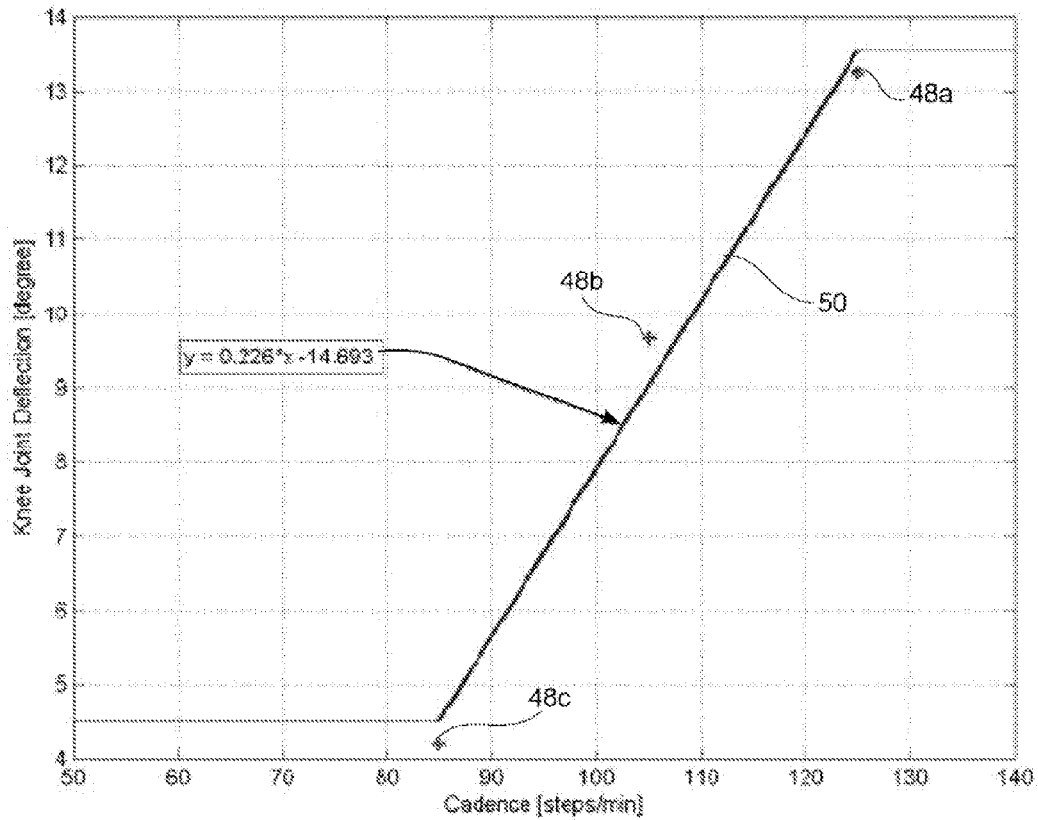
FIG. 19 is a plot of the expected deflection vs. cadence.

Using the numerical data provided in Table 5, the knee joint expected deflection as function of the gait cadence can be plotted to extract a relationship between both variables. Expressing the joint deflection as a function of the gait cadence is sustained by the fact that, for a given body weight, knee joint dynamic loading imposed by upper-body inertia increases with cadence. It then seems natural to relate both quantities using a simple relation or model. Referring to FIG. 19, there is shown a plot of the expected deflection vs. cadence for the data presented in Table 5, which are identified as points 48a, 48b and 48c.

From FIG. 19, it can be observed that the data points 48a, 48b and 48c roughly define a linear relation between the expected deflection and the cadence. A linear regression of the data points provided from the analysis of Winter's data for the 85 to 125 steps/min cadence range, i.e. points 48a, 48b and 48c on FIG. 19 can be performed. The resulting linear regression line 50 can be expressed numerically as:

$$y[\deg] = 0.226 * x\left[\frac{\text{steps}}{\min}\right] - 14.693. \quad \text{Equation 31}$$

The 85 to 125 steps/min cadence range is defined by Winter's data, which is provided for three discrete cadence values: 85, 105, and 125 steps/min. Outside of this range, expected deflection values can be saturated to a constant value corresponding to the last value computed in the cadence range. However, this definition of the expected deflection outside the known cadence range is not necessary, and other variants can be used. For example, measured kinematics behavior of the knee joint in the POD system operational cadence range of a user can be used to establish a more precise relation between the deflection under loading and the measured gait cadence for the complete cadence range of that user. Alternatively, additional data, other than Winter's data, can be used to determine an appropriate relationship between the deflection under loading and the measured gait cadence.

Tolerance

The tolerance parameter affects the performance and convergence speed of the tuning process of the dynamic gain tuner 135. To reflect the inter-subject variability included in Winter's kinematics data using the tolerance parameter, Winter's kinematics data standard deviation can be used to quantify the amplitude of a physically-relevant tolerance parameter. As mentioned previously, other kinematics data, other than Winter's kinematics data can be used.

The tolerance required in order to reproduce the one standard deviation boundaries found in Winter's data can be computed using:

$$\text{tolerance}[\%] = \frac{(((\theta_W + \sigma_{\theta W}) - \theta_{EP}) - y)[\deg]}{y[\deg]} * 100, \quad \text{Equation 32}$$

where
$\theta_W$ is Winter's mean angle at maximum deflection under loading;
$\sigma_{\theta W}$ is the corresponding standard deviation;
$\theta_{EP}$ is the equilibrium point position; and
y is the expected deflection computed from Equation 31.

Performing the computation for the values provided in Table 6 leads to the tolerance values specified in Table 7.

TABLE 7

Tolerance Values Computed from Winter's Kinematics Data One σ Boundaries

| Cadence steps/min | Winter's Means degree | Winter's σ degree | Equilibrium Point degree | Expected Deflection degree | Tolerance % |
|---|---|---|---|---|---|
| 85 | 16.2 | +6.73 | 12 | 4.52 | 141.8 |
|  |  | −6.73 |  |  | −155.97 |
| 105 | 21.7 | +5.34 |  | 9.04 | 66.37 |
|  |  | −5.34 |  |  | −51.77 |
| 125 | 25.2 | +4.94 |  | 13.56 | 33.78 |
|  |  | −4.94 |  |  | −39.09 |

From Table 7, it can be observed that the tolerance values are taking both positive and negative signs. A positive tolerance value in the table represents a tolerance level located farther than the expected deflection, while a negative tolerance value in the table represents a tolerance level located somewhere under the expected deflection. The tolerance values found using the data provided in Table 7 are observed to decrease with increasing gait cadence, starting from a very high value (i.e., −155%) for the slow cadence to 35%-40% for the fast gait cadence case. It can be observed from the data displayed in Table 7 that the tolerance value can be expressed as a function of the gait cadence, similarly to what was done above for the expected deflection parameter. Alternatively, additional or other information can be used to select the tolerance levels.

Each individual possess a unique gait characteristics, which explains the magnitude of the standard deviation found when averaging kinematics data through a group of different subjects. Defining the expected deflection values from Winter's average kinematics data generates a reference gait pattern that may not be suited to the unique gait characteristics of the user of the motorized POD 200.

The tolerance parameter can be selected in such a way that the dynamic gain tuner 135 does not strictly attempt to enforce a position response more or less corresponding to Winter's kinematic gait characteristics. In one embodiment, a tolerance value specified in the 10% to 50% range can be used. Alternatively, the value of the tolerance parameter, as well as its effects on the performance of the motorized POD 200, can be assessed experimentally for a specific motorized POD 200, or can be calibrated for a specific user as an initial configuration parameter.

Maximum Deflection

The compensated proportional $K_{P-C}$ and derivative $K_{D-C}$ gains (or proportional $K_P$ and derivative $K_D$ gains) and the gain scaling factor $K_C$ can be determined such that the position response of the motorized POD 200 follows the characteristic pattern illustrated in FIG. 17, which is composed of a late swing inertial overshoot of the equilibrium trajectory 51, a stance phase under loading equilibrium trajectory overshoot 52, and a late stance elastic return overshoot of the trajectory 53. To detect and measure the maximum deflection 30, the characteristics of both the position response 36 and the equilibrium trajectory 38 can be used in order to identify the occurrence of each overshoot region 51, 52 and 53 and measure the corresponding maximum deflection 30. This can be accomplished using an overshoot detection and deflection quantification procedure implemented as a state machine where overshoot state transitions are triggered by the detection of the deflection signal zero crossing. The maximum deflection value from the equilibrium trajectory measured during the stance phase can be used to calculate the gain scaling factor.

Computation of the Gain Scaling Factor $K_C$

Referring to FIGS. 13, 14 and 15, Using the equilibrium trajectory 38 (see FIG. 17), the dynamic gain tuner 135 can be described as a position regulator for the stance phase of the gait cycle, where dynamic trajectory compensator 125 or equilibrium trajectory generator 120 gains (i.e. compensated proportional $K_{P-C}$ and derivative $K_{D-C}$ gains or proportional $K_P$ and derivative $K_D$ gains, respectively) are specified as input and position response deflection from its equilibrium point is found as output. Assuming that for certain environmental and operational contexts (i.e. gait cadence, gait style, etc.), the perturbation force profile affecting the motorized POD 200 behavior is relatively periodic, the system can be modeled in a quasi-static manner with a relation of the form of Equation 1, i.e. $\tau = K_\theta \cdot \Delta\theta$.

Using this system description, the dynamic gain tuner 135 tracks, in a relatively loose manner, the expected deflection value by varying the gain scaling factor $K_C$ as external perturbation torque amplitude changes with gait dynamics, user's body mass, or actual payload nature.

Defining the tuning process of the dynamic gain tuner 135 can include applying the relationship between the measured deflection and correction factor (i.e. gain scaling factor $K_C$) to the compensated proportional $K_{P-C}$ and derivative $K_{D-C}$ gains (or proportional $K_P$ and derivative $K_D$ gains). Using the model expressed by Equation 1 for this specific relation, it can be observed that the system can be linear in terms of correction factor and measured deflection. Hence, modifying the compensated proportional $K_{P-C}$ and derivative $K_{D-C}$ gains (or proportional $K_P$ and derivative $K_D$ gains) by a proportion equivalent to the deficit or excess of measured deflection with respect to the expected deflection value can provide a sufficient correction. The gain scaling factor $K_C$ can be computed as a function of the difference between the measured and expected deflection value, or mathematically expressed as:

$$K_C = F(\Delta\theta - \Delta\theta_{SP}). \qquad \text{Equation 33}$$

where $\Delta\theta$ is the difference between the measured position and the equilibrium position; and $\Delta\theta_{SP}$ is the difference between the kinematics reference and the equilibrium position.

The current system state of the motorized POD 200 at any point in time when the dynamic gain tuner 135 is used, can be defined by the measured deflection amplitude as well as the current value of the compensated proportional $K_{P-C}$ and derivative $K_{D-C}$ gains (or proportional $K_P$ and derivative $K_D$ gains) and gain scaling factor $K_C$. The tuning process of the dynamic gain tuner 135 can then be defined as a recursive process making use of the system state historic information. Moreover, the recursive formulation of the tuner process can also enable the tuner process to correct itself as gait cycle iterations are performed. Expressing an embodiment of the tuning process in mathematical terms leads to:

$$K_C(k) = K_C(k-1) * (\Delta(k)+1), \qquad \text{Equation 34}$$

where k is the discrete-time index;

$K_C(k-1)$ is the previous value of the gain scaling factor; and $$\Delta(k) = \frac{\Delta\theta(k) - \Delta\theta_{SP}(k)}{\Delta\theta_{SP}(k)}, \qquad \text{Equation 35}$$

In Equation 35, the deflection term (i.e. $\Delta\theta(k) - \Delta\theta_{SP}(k)$) is normalized with respect to the expected deflection value (i.e. $\Delta\theta_{SP}(k)$), the result of which is offset in Equation 34 by unity in order to presents a net gain or attenuation of the gain scaling factor $K_C$.

Tuning Process

Figure 20:
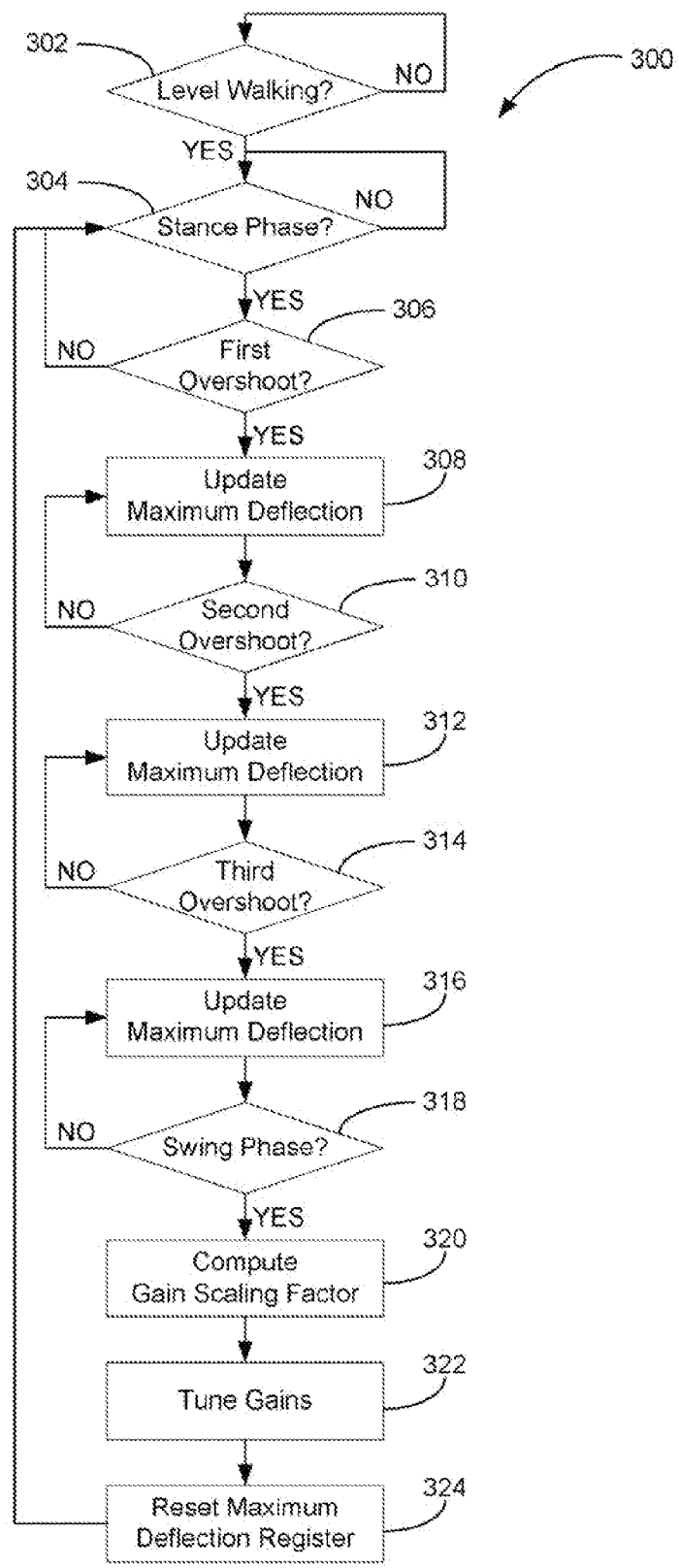
FIG. 20 is a flow diagram of a tuning process that may be executed by the dynamic gain tuner.

Referring to FIG. 20, there is shown a flow diagram of a tuning process 300 that may be executed by the dynamic gain tuner 135. The steps of the process 300 are indicated by blocks 302 to 324.

The process 300 starts at block 302 by verifying, from information received from the locomotion recognition module 110, whether the locomotion performed by the user of the motorized POD 200 is in a level walking state. If the user is in the level walking state, the process 300 proceeds to block 304, if not, the process 300 continues verifying if the user's locomotion is the level walking state.

At block 304, the process 300 verifies, using information received from the locomotion recognition module 110, whether the level walking state of locomotion of the user of the motorized POD 200 is in the stance phase. If the user is in the stance phase of the level walking state, the process 300 proceeds to block 306, if not, the process 300 continues verifying if the user's level walking state of locomotion is in the stance phase. The stance phase detection can be performed based on the velocity of the equilibrium trajectory, which is null during the stance phase. Alternatively, the stance phase detection can be performed using pressure sensors.

At block 306, the process 300 verifies whether the first expected overshoot of the position response of the motorized POD 200 is detected, e.g. overshoot region 51 of FIG. 17. In one embodiment, the process 300 detects the first overshoot when the previous locomotion state of the user is found to be the swing state combined with a current negative deflection value. If the process 300 detects the first overshoot, the process 300 proceeds to block 308, if not, the process 300 proceeds to block 304.

At block 308, the process 300 computes the current deflection and a register containing the maximum deflection value is updated if the current deflection value is superior to the value that is stored in the register.

At block 310, the process 300 verifies whether the second expected overshoot of the position response of the motorized POD 200 is detected, e.g. overshoot region 52 of FIG. 17. In one embodiment, the process 300 detects the second overshoot when a deflection signal zero crossing is detected. If a deflection signal zero crossing is detected, the process 300 proceeds to block 312, if not, the process proceeds to block 308.

At block 312, having detected the second overshoot, the process 300 computes the current deflection and the register containing the maximum deflection value is updated if the current deflection value is superior to the value that is stored in the register.

At block 314, the process 300 verifies whether the third expected overshoot of the position response of the motorized POD 200 is detected, e.g. overshoot region 53 of FIG. 17. In one embodiment, the process 300 detects the third overshoot when a deflection signal zero crossing is detected. If a deflection signal zero crossing is detected, the process 300 proceeds to block 316, if not, the process 300 proceeds to block 312.

At block 316, having detected the third overshoot, the process 300 computes the current deflection and the register containing the maximum deflection value is updated if the current deflection value is superior to the value that is stored in the register.

At block 318, the process 300 verifies whether the end of the third overshoot is detected, e.g. all three overshoots 51, 52, 53 of FIG. 17 have been considered. In one embodiment, the process 300 detects the end of the third overshoot when the swing phase is detected, which may be accomplished from information received from the locomotion recognition module 110. If the end of the third overshoot is detected, the process 300 proceeds to block 320, if not, the process 300 proceeds to block 316.

Having measured the maximum deflection, the process 300, at block 320, computes the gain scaling factor $K_C$ using Equation 34 at the point of maximum deflection with the initial value of $K_C$ being set to 1. As mentioned previously, although described using maximum deflection, any other predetermined point can be used to compute the gain scaling factor.

At block 322 the process 300 tunes the compensated proportional $K_{P-C}$ and derivative $K_{D-C}$ gains (or proportional $K_P$ and derivative $K_D$ gains). In one embodiment, the process 300 tunes the compensated proportional $K_{P-C}$ and derivative $K_{D-C}$ gains (or proportional $K_P$ and derivative $K_D$ gains) by multiplying them by the gain scaling factor $K_C$ computed at block 320.

Finally, at block 322, the maximum deflection register is reset and the process 300 proceeds back to block 302. Although illustrated as occurring at the end of the process 300, the reset can occur at other times, such as the beginning of the process (prior to block 302), prior to measuring the first overshoot (between blocks 304 and 306), and the like.

In an alternative embodiment, since it can be assumed that the maximum deflection under loading during the second overshoot (overshoot region 52 of FIG. 17) provides a valid performance measure for the overall stance phase system behavior, process 300 limit the measurement of the maximum deflection to within the second overshoot. A similar process can be used for other locomotion types, for example, ascending and descending stairs.

Although described by way of particular non-limiting illustrative embodiments and examples thereof, it should be noted that it will be apparent to persons skilled in the art that modifications may be applied to the particular embodiments described herein without departing from the scope of the disclosure.

Systems, modules, and controls described herein may comprise software, firmware, hardware, or any combination(s) of software, firmware, or hardware suitable for the purposes described herein. Software and other modules may reside on microcontrollers, microprocessors, and other devices suitable for the purposes described herein.

Embodiments are also described above with reference to flow chart illustrations and/or block diagrams of methods, apparatus (systems) and computer program products. It will be understood that each block of the flow chart illustrations and/or block diagrams, and combinations of blocks in the flow chart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flow chart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide steps for implementing the acts specified in the flow chart and/or block diagram block or blocks.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

The invention claimed is:

1. A method of controlling a motorized prosthetic or orthotic device provided with a joint, the method comprising:
   measuring a joint angle of a joint of a motorized prosthetic or orthotic device during a gait cycle;
   determining one or more control signals that control a stiffness of one or more actuators of the motorized prosthetic or orthotic device based at least on a difference of the measured joint angle from an equilibrium joint angle during stance phase of the gait cycle, wherein the equilibrium joint angle is approximately constant during at least a majority of the stance phase; and
   transmitting the one or more control signals to the one or more actuators to control the stiffness of the one or more actuators.

2. The method of claim 1, wherein the equilibrium joint angle is determined using a regression line of torque-angle during stance phase of a gait cycle.

3. The method of claim 1, wherein the equilibrium joint angle during the stance phase is different from an expected joint angle during the stance phase.

4. The method of claim 3, further comprising:
   altering the one or more control signals upon determining that a difference between the measured joint angle and the expected joint angle satisfies a threshold tolerance level; and
   transmitting the one or more altered control signals to the one or more actuators to alter the stiffness of the one or more actuators.

5. The method of claim 3, wherein the expected joint angle is calculated using Winter's kinematic data.

6. The method of claim 1, wherein the stiffness of the one or more actuators causes the measured joint angle to approximate a kinematic reference model during the stance phase.

7. The method of claim 6, wherein the kinematic reference model is Winter's Reference Trajectory.

8. The method of claim 1, wherein the one or more control signals are based on at least a position set-point, a proportional gain, and a derivative gain.

9. The method of claim 1, wherein the one or more control signals are based on one or more control parameters that are generated based on general characteristics of human locomotion using non-complex mathematical relationships.

10. The method of claim 9, wherein the one or more control parameters comprise at least one of a desired position, a proportional gain, and a derivative gain.

11. The method of claim 1, wherein the one or more control signals are determined based on least one of body mass and weight.

12. The method of claim 1, wherein the one or more control signals are updated between gait cycles during movement of the user.

13. The method of claim 1, wherein the measured joint angle is a maximum joint angle during the stance phase.

14. The method of claim 1, wherein the equilibrium joint angle changes during the stance phase.

* * * * *

UNITED STATES PATENT AND TRADEMARK OFFICE
CERTIFICATE OF CORRECTION

PATENT NO. : 9,060,884 B2  
APPLICATION NO. : 13/099961  
DATED : June 23, 2015  
INVENTOR(S) : David Langlois Page 1 of 1

It is certified that error appears in the above-identified patent and that said Letters Patent is hereby corrected as shown below:

In column 8 at line 4, Change "$K_{P-D}$" to --$K_{P-C}$--.

Signed and Sealed this  
Twenty-third Day of August, 2016

Michelle K. Lee  
*Director of the United States Patent and Trademark Office*